US011903749B2

(12) United States Patent
Zilberstien et al.

(10) Patent No.: US 11,903,749 B2
(45) Date of Patent: Feb. 20, 2024

(54) NUCLEAR MEDICINE TOMOGRAPHY SYSTEM COMPRISING A DETECTOR CARRIER HOUSING AND A HEAT PUMP CONFIGURED TO COOL AIR WITHIN THE DETECTOR CARRIER HOUSING

(71) Applicant: Spectrum Dynamics Medical Limited, Road Town (VG)

(72) Inventors: Yoel Zilberstien, Herzlia (IL); Nathaniel Roth, Tel-Aviv (IL); Idan Fogel, Natania (IL)

(73) Assignee: Spectrum Dynamics Medical Limited, Road Town (VG)

( * ) Notice: Subject to any disclaimer, the term of this patent is extended or adjusted under 35 U.S.C. 154(b) by 658 days.

(21) Appl. No.: 16/756,520

(22) PCT Filed: Oct. 18, 2018

(86) PCT No.: PCT/IB2018/058102
§ 371 (c)(1),
(2) Date: Apr. 16, 2020

(87) PCT Pub. No.: WO2019/077548
PCT Pub. Date: Apr. 25, 2019

(65) Prior Publication Data
US 2020/0289074 A1  Sep. 17, 2020

Related U.S. Application Data

(60) Provisional application No. 62/574,345, filed on Oct. 19, 2017.

(51) Int. Cl.
*A61B 6/00* (2006.01)
*A61B 6/03* (2006.01)
(Continued)

(52) U.S. Cl.
CPC .............. *A61B 6/037* (2013.01); *A61B 6/025* (2013.01); *A61B 6/03* (2013.01); *A61B 6/032* (2013.01);
(Continued)

(58) Field of Classification Search
CPC ........... A61B 6/03; A61B 6/032; A61B 6/035; A61B 6/037; A61B 6/42; A61B 6/4208;
(Continued)

(56) References Cited

U.S. PATENT DOCUMENTS 3,902,070 A  8/1975 Amor, Jr. et al.
4,057,726 A  11/1977 Jaszczak
(Continued)

FOREIGN PATENT DOCUMENTS

EP         0 283 870        10/1990
WO    WO 2013/168111       11/2013
(Continued)

OTHER PUBLICATIONS

Official Action dated Feb. 14, 2022 from US Patent and Trademark Office Re. U.S. Appl. No. 17/120,394. (32 pages).
(Continued)

*Primary Examiner* — Allen C. Ho

(57) ABSTRACT

A nuclear medicine tomography system including: a detector carrier; a detector carrier housing including an inner space; a plurality of detector units, coupled to the detector carrier, each detector unit comprising: a detector camera; a cooling channel which guides air to the detector camera from the inner space; an exhaust channel which guides air from the detector camera to the inner space; a heat pump configured to cool air within the inner space.

19 Claims, 19 Drawing Sheets

(51) Int. Cl.
    *G01T 1/16* (2006.01)
    *G01T 1/29* (2006.01)
    *G01T 1/164* (2006.01)
    *A61B 6/02* (2006.01)
    *G01T 1/20* (2006.01)
    *G01T 1/24* (2006.01)
    *G05D 23/19* (2006.01)

(52) U.S. Cl.
    CPC ............... *A61B 6/035* (2013.01); *A61B 6/42* (2013.01); *A61B 6/4208* (2013.01); *A61B 6/4225* (2013.01); *A61B 6/4258* (2013.01); *A61B 6/4266* (2013.01); *A61B 6/4275* (2013.01); *A61B 6/44* (2013.01); *A61B 6/4429* (2013.01); *A61B 6/4435* (2013.01); *A61B 6/4441* (2013.01); *A61B 6/4447* (2013.01); *A61B 6/4488* (2013.01); *G01T 1/1648* (2013.01); *G01T 1/20188* (2020.05); *G01T 1/20189* (2020.05); *G01T 1/244* (2013.01); *G01T 1/2985* (2013.01); *G05D 23/1932* (2013.01)

(58) Field of Classification Search
    CPC ... A61B 6/4225; A61B 6/4233; A61B 6/4241; A61B 6/4258; A61B 6/4266; A61B 6/4275; A61B 6/44; A61B 6/4429; A61B 6/4435; A61B 6/4441; A61B 6/4447; A61B 6/4488; G01T 1/29; G01T 1/2907; G01T 1/2914; G01T 1/2921; G01T 1/2928; G01T 1/2935; G01T 1/2978; G01T 1/2985; G01T 1/16; G01T 1/1603; G01T 1/1606
    USPC ............... 378/4, 19, 98.8, 189, 204, 62, 63; 250/370.09, 363.02, 363.03, 363.04, 250/363.05
    See application file for complete search history.

(56) References Cited

U.S. PATENT DOCUMENTS

| | | | |
|---|---|---|---|
| 4,209,700 A | 6/1980 | Stoddart | |
| 5,982,843 A * | 11/1999 | Bailey | A61B 6/035 378/4 |
| 6,140,650 A | 10/2000 | Berlad | |
| 6,188,743 B1 | 2/2001 | Tybinkowski et al. | |
| 6,212,251 B1 | 4/2001 | Tomura et al. | |
| 6,242,743 B1 | 6/2001 | DeVito et al. | |
| 6,472,668 B1 * | 10/2002 | Griesmer | G01T 1/1644 250/338.4 |
| 6,583,420 B1 | 6/2003 | Nelson | A61B 6/4258 250/397 |
| 6,988,827 B2 * | 1/2006 | Mueller | G01T 1/2985 378/199 |
| 7,030,387 B2 * | 4/2006 | Serebryanov | G01T 1/1648 250/370.15 |
| 7,201,515 B2 * | 4/2007 | Lacey | A61B 6/4488 378/199 |
| 7,262,415 B2 * | 8/2007 | Crosetto | A61B 6/037 250/363.04 |
| 7,342,234 B2 * | 3/2008 | Yanagita | G01T 1/244 250/370.15 |
| 7,488,949 B2 * | 2/2009 | Ueno | A61B 6/4488 250/370.15 |
| 7,511,277 B2 * | 3/2009 | Ueno | A61B 6/037 250/363.04 |
| 7,573,040 B2 * | 8/2009 | Tkaczyk | G01T 1/242 250/370.09 |
| 7,592,597 B2 | 9/2009 | Hefetz et al. | |
| 7,755,057 B2 * | 7/2010 | Kim | G01T 1/1644 250/497.1 |
| 7,772,559 B2 * | 8/2010 | Burbar | G01T 1/1603 250/363.03 |
| 8,269,176 B2 * | 9/2012 | D'Ambrosio | G01T 1/161 250/361 R |
| 8,338,788 B2 * | 12/2012 | Zilberstein | A61B 6/04 250/363.04 |
| 8,378,677 B2 * | 2/2013 | Morich | G01T 1/1603 324/307 |
| 8,409,092 B2 * | 4/2013 | Canzolino | A61B 6/045 600/407 |
| 8,476,594 B2 * | 7/2013 | Frach | G01T 1/2985 250/363.04 |
| 8,481,949 B2 * | 7/2013 | Martin | A61B 6/4488 250/363.03 |
| 8,492,725 B2 | 7/2013 | Zilberstein et al. | |
| 8,699,660 B2 * | 4/2014 | Joshi | G05D 23/1931 378/19 |
| 8,748,827 B2 | 6/2014 | Zilberstein et al. | |
| 8,987,673 B2 * | 3/2015 | Niederlöhner | G01T 1/1641 250/363.03 |
| 9,029,791 B1 * | 5/2015 | Kovalski | A61B 6/037 250/369 |
| 9,057,788 B2 | 6/2015 | Abraham | G01T 1/1647 |
| 9,173,618 B2 * | 11/2015 | Hermony | G01T 1/1614 |
| 9,295,439 B2 * | 3/2016 | Hefetz | A61B 6/037 |
| 9,513,236 B2 * | 12/2016 | Kawaguchi | A61B 6/032 |
| 9,579,072 B1 * | 2/2017 | Grobshtein | A61B 6/465 |
| 9,599,490 B2 * | 3/2017 | Khen | G01D 11/245 |
| 9,606,245 B1 | 3/2017 | Czarnecki et al. | |
| 9,662,079 B2 * | 5/2017 | Rafaeli | A61B 6/0407 |
| 9,700,273 B2 * | 7/2017 | Lacey | A61B 6/035 |
| 9,820,708 B2 * | 11/2017 | Risher-Kelly | H02K 7/108 |
| 9,869,647 B2 * | 1/2018 | Featonby | G01N 23/046 |
| 9,903,964 B2 * | 2/2018 | Thran | G01T 7/005 |
| 9,924,915 B2 * | 3/2018 | Kodaira | F24F 13/081 |
| 10,054,698 B2 * | 8/2018 | Hefetz | A61B 6/035 |
| 10,143,437 B2 * | 12/2018 | Hefetz | A61B 6/52 |
| 10,178,976 B2 * | 1/2019 | Liu | F28F 3/12 |
| 10,253,903 B2 * | 4/2019 | Fujimoto | F16K 47/04 |
| 10,267,930 B2 * | 4/2019 | Su | G01T 1/2985 |
| 10,326,561 B2 * | 6/2019 | Dudek | H02K 1/22 |
| 10,441,816 B2 * | 10/2019 | Liu | A61N 5/1049 |
| 10,478,133 B2 * | 11/2019 | Levy | A61B 6/585 |
| 10,488,533 B2 * | 11/2019 | Liu | G01T 1/244 |
| 10,542,228 B2 * | 1/2020 | Nozawa | H04N 5/374 |
| 10,575,802 B2 * | 3/2020 | Bouhnik | A61B 6/4291 |
| 10,624,596 B2 * | 4/2020 | Gregerson | A61B 6/00 |
| 10,663,608 B2 * | 5/2020 | Lyu | G01T 7/005 |
| 10,716,955 B2 * | 7/2020 | Kuang | A61N 5/1049 |
| 10,772,590 B2 * | 9/2020 | Arber | A61B 6/035 |
| 10,863,956 B2 * | 12/2020 | Zilberstien | A61B 6/04 |
| 10,987,069 B2 * | 4/2021 | Roth | A61B 6/0407 |
| 11,006,911 B2 * | 5/2021 | Liu | G01T 1/2985 |
| 11,020,074 B2 * | 6/2021 | Kenig | A61B 5/0064 |
| 11,255,987 B2 * | 2/2022 | Roth | G06T 7/80 |
| 11,311,254 B2 * | 4/2022 | Okuno | A61B 6/102 |
| 11,337,660 B2 * | 5/2022 | Zilberstien | A61B 6/105 |
| 11,585,953 B2 * | 2/2023 | Ye | G01T 1/2018 |
| 2003/0209662 A1 | 11/2003 | Nelson et al. | |
| 2005/0017182 A1 | 1/2005 | Joung et al. | |
| 2008/0217541 A1 | 9/2008 | Kim | |
| 2008/0230709 A1 | 9/2008 | Tkaczyk et al. | |
| 2010/0061509 A1 | 3/2010 | D'Ambrosio et al. | |
| 2010/0188082 A1 | 7/2010 | Morich et al. | |
| 2011/0026685 A1 | 2/2011 | Zilberstein et al. | |
| 2011/0103544 A1 | 5/2011 | Hermony | |
| 2013/0168567 A1 | 7/2013 | Wartski et al. | |
| 2013/0200269 A1 | 8/2013 | Abraham et al. | |
| 2015/0028218 A1 | 1/2015 | Kataoka et al. | |
| 2015/0065874 A1 | 3/2015 | Rafaeli et al. | |
| 2015/0094571 A1 | 4/2015 | Bouhnik et al. | |
| 2015/0119704 A1 | 4/2015 | Roth et al. | |
| 2015/0276949 A1 | 10/2015 | Grobshtein et al. | |
| 2015/0342543 A1 | 12/2015 | Khen et al. | |
| 2016/0007941 A1 | 1/2016 | Hefetz | |
| 2016/0282153 A1 | 9/2016 | Hefetz et al. | |
| 2016/0287197 A1 | 10/2016 | Risher-Kelly et al. | |
| 2016/0313263 A1 | 10/2016 | Featonby et al. | |

(56) References Cited

U.S. PATENT DOCUMENTS

| | | |
|---|---|---|
| 2016/0380728 A1 | 12/2016 | Dudek et al. |
| 2017/0014096 A1 | 1/2017 | Bouhnik et al. |
| 2017/0045632 A1 | 2/2017 | Thran |
| 2017/0082759 A1 | 3/2017 | Lyu et al. |
| 2017/0112454 A1 | 4/2017 | Yun et al. |
| 2017/0153338 A1 | 6/2017 | Kovalski et al. |
| 2017/0189720 A1 | 7/2017 | Liu et al. |
| 2017/0332025 A1 | 11/2017 | Nozawa et al. |
| 2017/0370499 A1 | 12/2017 | Fujimoto et al. |
| 2018/0059270 A1 | 3/2018 | Hefetz et al. |
| 2018/0110496 A1 | 4/2018 | Levy et al. |
| 2018/0236267 A1 | 8/2018 | Kuang et al. |
| 2020/0163631 A1 | 5/2020 | Okuno |
| 2020/0281546 A1 | 9/2020 | Zilberstien et al. |
| 2020/0297296 A1 | 9/2020 | Zilberstien et al. |
| 2020/0301033 A1 | 9/2020 | Roth et al. |
| 2021/0093270 A1 | 4/2021 | Zilberstien et al. |
| 2022/0179109 A1 | 6/2022 | Roth |
| 2023/0028049 A1 | 1/2023 | Zilberstien et al. |

FOREIGN PATENT DOCUMENTS

| | | |
|---|---|---|
| WO | WO 2019/077542 | 4/2019 |
| WO | WO 2019/077542 A3 | 4/2019 |
| WO | WO 2019/077544 | 4/2019 |
| WO | WO 2019/077548 | 4/2019 |
| WO | WO 2019/077548 A3 | 4/2019 |
| WO | WO 2019/077552 | 4/2019 |

OTHER PUBLICATIONS

Official Action dated Jul. 7, 2021 from the US Patent and Trademark Office Re. U.S. Appl. No. 16/756,496. (12 pages).
Supplementary European Search Report and the European Search Opinion dated Jul. 14, 2021 From the European Patent Office Re. Application No. 18869177.8. (8 Pages).
Official Action dated Sep. 9, 2020 from the US Patent and Trademark Office Re. U.S. Appl. No. 16/756,496. (27 pages).
Interview Summary dated Mar. 19, 2021 From the US Patent and Trademark Office Re. U.S. Appl. No. 16/756,496. (2 Pages).
Supplementary European Search Report and the European Search Opinion dated Jun. 4, 2021 From the European Patent Office Re. Application No. 18868897.2. (7 Pages).
Supplementary European Search Report and the European Search Opinion dated Jun. 21, 2021 From the European Patent Office Re. Application No. 18869300.6. (8 Pages).
Final Official Action dated Feb. 23, 2021 From the US Patent and Trademark Office Re. U.S. Appl. No. 16/756,496. (25 Pages).
Restriction Official Action dated Apr. 2, 2021 From the US Patent and Trademark Office Re. U.S. Appl. No. 16/756,511. (6 Pages).
International Preliminary Report on Patentability dated Apr. 30, 2020 From the International Bureau of WIPO Re. Application No. PCT/IB2018/058067. (6 Pages).
International Preliminary Report on Patentability dated Apr. 30, 2020 From the International Bureau of WIPO Re. Application No. PCT/IB2018/058094. (7 Pages).
International Preliminary Report on Patentability dated Apr. 30, 2020 From the International Bureau of WIPO Re. Application No. PCT/IB2018/058102. (8 Pages).
International Preliminary Report on Patentability dated Apr. 30, 2020 From the International Bureau of WIPO Re. Application No. PCT/IB2018/058108. (10 Pages).
International Search Report and the Written Opinion dated Apr. 23, 2019 From the International Searching Authority Re. Application No. PCT/IB2018/058108. (20 Pages).
International Search Report and the Written Opinion dated Apr. 24, 2019 From the International Searching Authority Re. Application No. PCT/IB2018/058094. (15 Pages).
International Search Report and the Written Opinion dated Apr. 24, 2019 From the International Searching Authority Re. Application No. PCT/IB2018/058102. (16 Pages).
International Search Report and the Written Opinion dated Feb. 25, 2019 From the International Searching Authority Re. Application No. PCT/IB2018/058067. (12 Pages).
Invitation to Pay Additional Fees dated Feb. 7, 2019 From the International Searching Authority Re. Application No. PCT/IB2018/058094. (2 Pages).
Invitation to Pay Additional Fees dated Feb. 7, 2019 From the International Searching Authority Re. Application No. PCT/IB2018/058102. (3 Pages).
Invitation to Pay Additional Fees dated Feb. 7, 2019 From the International Searching Authority Re. Application No. PCT/IB2018/058108. (2 Pages).
Notice of Allowance dated Aug. 12, 2020 from the US Patent and Trademark Office Re. U.S. Appl. No. 16/756,492. (9 pages).
Final Office Action dated Sep. 20, 2021 from the US Patent and Trademark Office Re. U.S. Appl. No. 16/756,511. (26 pages).
Almeida Silva Salvado "Evaluation of the D-SPECT System: Geometry Considerations and Respiratory Motion", Dissertação Mestrado Integrado em Engenharia Biomédica e Biofísica, Perfil de Radiações em Diagnóstico e Terapia [Dissertation Integrated Master in Biomedical Engineering and Biophysics, Radiation Profile in Diagnosis and Therapy], Universidade de Lisboa, Portugal, Faculdade de Ciências Departamento de Física, 134 P., 2012.
Barrento Da Costa "Evaluation of the D-SPECT System: Region Centric Acquisition and Tracer Kinetics", Dissertação Mestrado Integrado em Engenharia Biomédica e Biofísica [Dissertation Integrated Master in Biomedical Engineering and Biophysics], Universidade de Lisboa, Portugal, Faculdade de Ciências, Departamento de Física, 97 P., 2012.
Erlandsson et al. "Assessing Possible Use of CZT Technology for Application to Brain SPECT", 2011 IEEE Nuclear Science Symposium Conference Record, Valencia, Spain, Oct. 23-29, 2011, p. 3354-3358, Oct. 23, 2011.
Gambhir et al. "A Novel High-Sensitivity Rapid-Acquisition Single-Photon Cardiac Imaging Camera", The Journal of Nuclear Medicine, 50(4): 635-643, Apr. 2009.
Moore et al. "Improved Performance From Modifications to Multidetector SPECT Brain Scanner", The Journal of Nuclear Medicine, 25(6): 688-691, Jun. 1984.
Slomka et al. "Advances in Technical Aspects of Myocardial Perfusion SPECT Imaging", Journal of Nuclear Cardiology, 16(2): 255-276, Published Online Feb. 26, 2009.
Notice of Allowance dated Jan. 21, 2022 together eoth Interview Summary dated Jan. 6, 2022 from US Patent and Trademark Office Re. U.S. Appl. No. 16/756,511. (8 pages).
Notice of Allowance dated Jun. 1, 2022 from US Patent and Trademark Office Re. U.S. Appl. No. 17/120,394. (7 pages).
Official Action dated Jun. 10, 2021 From the US Patent and Trademark Office Re. U.S. Appl. No. 16/756,511. (31 Pages).
Supplementary European Search Report and the European Search Opinion dated Jun. 9, 2021 From the European Patent Office Re. Application No. 18868387.4. (7 Pages).

\* cited by examiner

NUCLEAR MEDICINE TOMOGRAPHY SYSTEM COMPRISING A DETECTOR CARRIER HOUSING AND A HEAT PUMP CONFIGURED TO COOL AIR WITHIN THE DETECTOR CARRIER HOUSING

RELATED APPLICATIONS

This application is related to U.S. Patent No. 10,987,069, U.S. Pat. Nos. 8,338,788, 8,492,725 and 8,748,827, the contents, which are incorporated by reference as if fully, set forth herein in their entirety.

This application is also related to co-filed, and co-assigned: to International Patent Application entitled "MOVING PARTS IN A NUCLEAR MEDICINE (N-M) IMAGING SYSTEM" which draws priority from U.S. Patent Application No. 62/574,277,

- to International Patent Application entitled "CALIBRATION AND QUALITY CONTROL OF A NUCLEAR-MEDICINE (N-M) RADIO IMAGING SYSTEM" which draws priority from U.S. Patent Application No. 62/574,300, and
- to International Patent Application entitled "SAFETY MECHANISMS FOR CLOSE RANGE TOMOGRAPHIC SCANNING MACHINE AND METHODS OF USE" which draws priority from U.S. Patent Application No. 62/574,294,
- the disclosure of which are incorporated herein by reference as if fully set forth herein in their entirety.

This application is related to U.S. Patent Publication No. 2015/0119704, U.S. Pat. Nos. 8,338,788, 8,492,725 and 8,748,827, the contents, which are incorporated by reference as if fully, set forth herein in their entirety.

FIELD AND BACKGROUND OF THE INVENTION

The present invention, in some embodiments thereof, relates to cooling of an imaging system and, more particularly, but not exclusively, to cooling of a nuclear medicine tomography system including a plurality of detector heads mounted on a detector carrier where the detector heads are translatable with respect to the detector carrier.

U.S. Pat. No. 5,982,843 discloses "A computed tomography (CT) scanner includes an enclosure which forms a substantially sealed chamber around the rotatable disk carrying the radiation source and the radiation detectors. The CT scanner further includes an air conditioning system for controlling the temperature and humidity of the air inside the chamber. The air conditioning system can be a closed loop system whereby only air from inside the chamber is processed through the air conditioning system and no outside air is introduced to the chamber. Thus, the CT scanner can be operated in a wider range of environmental conditions. In an alternate embodiment, the air conditioning system can produce a positive pressure inside the chamber to prevent outside air from entering through openings in the enclosure. In this embodiment, the air conditioning system can include an input port in order to draw sufficient outside air to produce a positive pressure inside the chamber. The input port can include a filter to prevent dust from entering the chamber, thus, enabling the CT scanner to have a longer useful life between preventative maintenance and service events."

SUMMARY OF THE INVENTION

According to an aspect of some embodiments of the present invention there is provided a nuclear medicine tomography system comprising:

a detector carrier;
a detector carrier housing including an inner space;
a plurality of detector units, coupled to the detector carrier, each detector unit comprising:
 a detector camera;
 a cooling channel, which guides air to the detector camera from the inner space;
 an exhaust channel, which guides air from the detector camera to the inner space;
a heat pump configured to cool air within the inner space.

According to some embodiments of the invention, each detector unit comprises an extendable arm in which each detector camera is housed;

wherein the cooling channel and the exhaust channel pass through the extendable arm.

According to some embodiments of the invention, the system comprises at least one actuator configured to generate air flow through one or both of the channels.

According to some embodiments of the invention, the at least one actuator drives a fan positioned to drive air through one or both of the channels.

According to some embodiments of the invention, the exhaust channel extends along a surface of the detector camera or a surface coupled to the detector camera.

According to some embodiments of the invention, the fan is located at an end of the detector camera and the fan drives air through the exhaust channel along the surface.

According to some embodiments of the invention, the system comprises a motor configured to actuate movement of the detector camera; and wherein the exhaust channel is shaped to increase volumetric fluid flow rate impinging on a surface thermally coupled to the motor.

According to some embodiments of the invention, the exhaust channel reduces in at least one dimension at least at one point along a length of the detector camera.

According to some embodiments of the invention, the system comprises a plurality of fans positioned to generate air flow through the exhaust channel towards the inner space.

According to some embodiments of the invention, the system comprises one or more actuator configured to generate air flow through the inner space from one or more inner space inlet towards one or more inner space outlet.

According to some embodiments of the invention, the one or more actuator drives one or more fan positioned to generate the air flow through the inner space.

According to some embodiments of the invention, the heat pump comprises a radiator cooler comprising a plurality of pipes through which fluid is circulated.

According to some embodiments of the invention, the heat pump comprises a portion located within the detector carrier housing.

According to some embodiments of the invention, the cooling channel and the exhaust channel are separated from each other.

According to some embodiments of the invention, the detector unit is separated from ambient air within a bore by a cover.

According to some embodiments of the invention, at least one of the detector units comprises a rotation actuator configured to rotate the detector camera of the at least one detector unit.

According to some embodiments of the invention, the rotation actuator is configured to rotate one or more fan coupled to the detector camera of the at least one detector unit.

According to some embodiments of the invention, the exhaust channel extends past the at least one rotation actuator.

According to some embodiments of the invention, at least one of detector units includes a layer of thermal insulation configured to reduce heat transfer to the detector camera of the at least one detector unit from a bore.

According to an aspect of some embodiments of the present invention there is provided an imaging system comprising:
- a detector carrier comprising a bore space into which at least a portion of a patient to be scanned is placed;
- a detector unit mounted on the detector carrier, the detector unit comprising a channel extending through the detector unit in a direction away from the bore space;
- at least one actuator connected to the detector unit and configured to generate air flow through the channel in the direction away from the bore.

According to some embodiments of the invention, the system comprises a plurality of the detector units, which detector units are each mounted to the detector carrier.

According to some embodiments of the invention, the channel includes a surface thermally coupled to the detector camera.

According to some embodiments of the invention, the camera is a gamma camera.

According to some embodiments of the invention, the channel includes a surface thermally coupled to a motor, which motor is configured to actuate movement of the detector unit with respect to the detector carrier.

According to some embodiments of the invention, the surface thermally coupled to the motor is a motor housing.

According to some embodiments of the invention, the motor is configured to actuate rotation of the detector unit.

According to some embodiments of the invention, the motor is configured to actuate oscillatory rotation of the detector unit.

According to some embodiments of the invention, the channel extends into an inner space within a housing of the detector carrier.

According to some embodiments of the invention, the system comprises at least one actuator configured to circulate air within the inner space.

According to some embodiments of the invention, at least one actuator is configured to generate air flow past a surface coupled to a power supply.

According to some embodiments of the invention, the at least one actuator is configured to generate air flow past a surface thermally coupled to a detector carrier motor configured to rotate the detector carrier within the detector carrier housing.

According to some embodiments of the invention, the system comprises one or more cooler configured to supply cooled air to the inner space.

According to some embodiments of the invention, the system comprises one or more heat exchanger configured to cool air within at least a portion of the inner space.

According to some embodiments of the invention, the system comprises comprising:
- at least one sensor configured to generate a measurement signal based on a temperature at one or more point within the detector unit;
- a processor configured to:
  - receive the measurement signal;
  - generate an actuator control signal, based on the measurement signal;
  - send the actuator control signal to the actuator.

According to some embodiments of the invention, the at least one actuator is configured to generate air flow from the bore and through the channel in the direction away from the bore.

According to some embodiments of the invention, the actuator is configured to increase heat transfer at a heat exchanger.

According to some embodiments of the invention, the actuator is configured to decrease temperature of air inserted into the detector carrier housing.

According to some embodiments of the invention, the system comprises a detector unit cover separating the detector unit from ambient air.

According to some embodiments of the invention, air flows into the cover from the inner space, returning to the inner space through the channel.

According to an aspect of some embodiments of the present invention there is provided a nuclear medicine tomography system comprising:
- a detector carrier;
- a detector carrier housing including an inner space;
- a plurality of detector units coupled to the detector carrier, each detector unit comprising:
  - a detector camera;
  - a cooling system including at least a portion located within a space into which at least a portion of a patient to be scanned is placed.

According to some embodiments of the invention, the cooling system includes a channel, which guides air from the detector camera to the inner space.

According to some embodiments of the invention, the cooling system includes a fan positioned to generate air flow from the detector camera to the inner space.

According to an aspect of some embodiments of the present invention there is provided an imaging system comprising:
- a detector carrier;
- a plurality of detector units each coupled to the detector carrier and movable with respect to the detector carrier, each detector unit comprising: at least one sensor configured to generate a measurement signal based on a temperature at one or more point within the detector unit;
- a processor configured to:
  - receive a measurement signal from each sensor;
  - generate and send a control signal to an actuator configured to cool one or more portion of the system.

According to some embodiments of the invention, the at least one sensor is configured to generate a measurement signal based on a temperature of a portion of the detector unit within a bore.

According to some embodiments of the invention, the processor is configured to generate and send control signals to a plurality of actuators, at least one actuator configured to cool each detector unit.

According to some embodiments of the invention, the processor is configured to generate a control signal for each detector unit, based on a measurement signal from at least one sensor associated with the detector unit, and to send the control signal to an actuator associated with the detector unit.

According to some embodiments of the invention, each detector comprises an actuator configured to actuate a fan.

According to an aspect of some embodiments of the present invention there is provided a method of nuclear medicine tomography system temperature regulation comprising:

measuring temperature at one or more point within the system;

adjusting speed of air flow within one or more of a plurality of detector units, based on the measured temperature, where each detector unit is mounted on a detector carrier and comprises a detector array, to maintain a temperature of the detector arrays below a threshold temperature.

According to some embodiments of the invention, the measuring comprises measuring temperature within the detector unit.

According to some embodiments of the invention, the measuring comprises measuring temperature within more than one detector unit comprising a detector camera;
wherein the adjusting comprises adjusting a speed of air flow within more than one detector unit.

According to some embodiments of the invention, the adjusting comprises adjusting a speed of air flow within a housing of the detector carrier.

According to some embodiments of the invention, the measuring comprises measuring temperature at one or more point within an inner space of a detector carrier housing.

According to some embodiments of the invention, wherein the adjusting comprises adjusting a temperature of air flow into an inner space of a detector carrier housing from a cooler.

According to some embodiments of the invention, wherein the adjusting comprises adjusting a speed of one or more fan.

According to some embodiments of the invention, the method comprises, comprising measuring temperature at one or more point within a room housing the system, outside the housing of the detector carrier; and
adjusting one or more cooler actuator to maintain a temperature of the room within a temperature range, where the temperature range is selected for patient comfort.

According to some embodiments of the invention, the threshold temperature is below a lowest bound of the temperature range.

According to an aspect of some embodiments of the present invention there is provided a method of setting a room temperature comprising:
setting a desired room temperature, which is above a threshold temperature and is selected for patient comfort;
setting a nuclear medicine tomography system detector camera desired temperature, which is selected for low noise of the detector camera and is below the desired room temperature.

According to an aspect of some embodiments of the present invention there is provided an imaging system comprising:
a plurality of detector cameras;
at least one sensor configured to generate a signal based on a temperature at one or more point within the system;
a processor comprising circuitry configured to:
send a first control signal to at least one actuator configured to maintain a temperature of the detector cameras below a threshold temperature;
send a second control signal configured to control to at least one actuator of a room temperature regulator configured to control a room temperature of a room in which the system is located, to maintain the room temperature within a temperature range selected for patient comfort.

According to some embodiments of the invention, the threshold temperature is below the temperature range.

According to some embodiments of the invention, wherein the room temperature regulator is an air conditioner including an outlet into the room.

According to some embodiments of the invention, the system comprises at least one room sensor configured to generate a room sensor signal based on a temperature of the room;
wherein the second control signal is based on the room sensor signal.

According to some embodiments of the invention, the system comprises a detector carrier located within the detector housing; and
a plurality of detector units, each unit comprising:
a chassis coupled to the detector carrier;
an extendable arm coupled to the chassis and extendable from the chassis towards a bore of the detector carrier; and
one of the detector cameras mounted to the extendable arm.

According to some embodiments of the invention, each detector unit comprises a fan configured to generate air flow past the detector carrier towards the housing inner space.

According to some embodiments of the invention, the system comprises at least one fan configured to circulate air within the housing inner space.

According to an aspect of some embodiments of the present invention there is provided an imaging system comprising:
at least two movable detector camera units, including a first detector camera unit and a second detector camera unit;
a controller configured to move the first detector unit and the second detector into close proximity, where the first detector unit comprises:
a detector camera; and
a heat sink including a portion, which extends away from the camera, the portion of the heat sink having reduced volume at one or more edge thereby allowing the controller to move detector camera of the first detector unit closer to the second detector camera unit.

According to some embodiments of the invention, the detector camera of the first detector unit is rotatable about at least one axis of rotation.

According to some embodiments of the invention, rotation of the detector camera of the first detector unit moves the edge with respect to the second detector unit.

According to some embodiments of the invention, the second detector unit comprises a detector camera and a heat sink according to the detector camera of the first detector unit.

According to some embodiments of the invention, the heat sink comprises a base coupled to the detector camera, where a cross sectional shape of the heat sink comprises:
a first edge region, which extends to a first edge region height above the base;
a second edge region which extends to a second edge region height above the base; and
a central region disposed between the first edge region and the second edge region, which central region extends to a central region height, which is taller than one or both of the edge region heights.

According to some embodiments of the invention, a cross sectional shape of the heat sink is an arc of a circle where the circle is centered about the axis of rotation.

According to some embodiments of the invention, the detector camera is elongate and the axis of rotation is parallel to a central long axis of the camera.

According to some embodiments of the invention, the heat sink includes a plurality of fins separated by inlets and extending from a base.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system."

Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In some cases, elements in corresponding figures have corresponding numbers, which are not necessarily explicitly described. For example, element 104 in FIG. 1A corresponds to element 204 in FIG. 2A, which may not be explicitly described.

In the drawings:

FIGS. 1A-B are simplified schematics of a nuclear medicine topography system (NMTS), according to some embodiments of the invention;

FIGS. 1C-D are simplified schematics of a detector unit, according to some embodiments of the invention;

FIG. 2A is a simplified schematic of air flow within an imaging system, according to some embodiments of the invention;

Figure 7A:
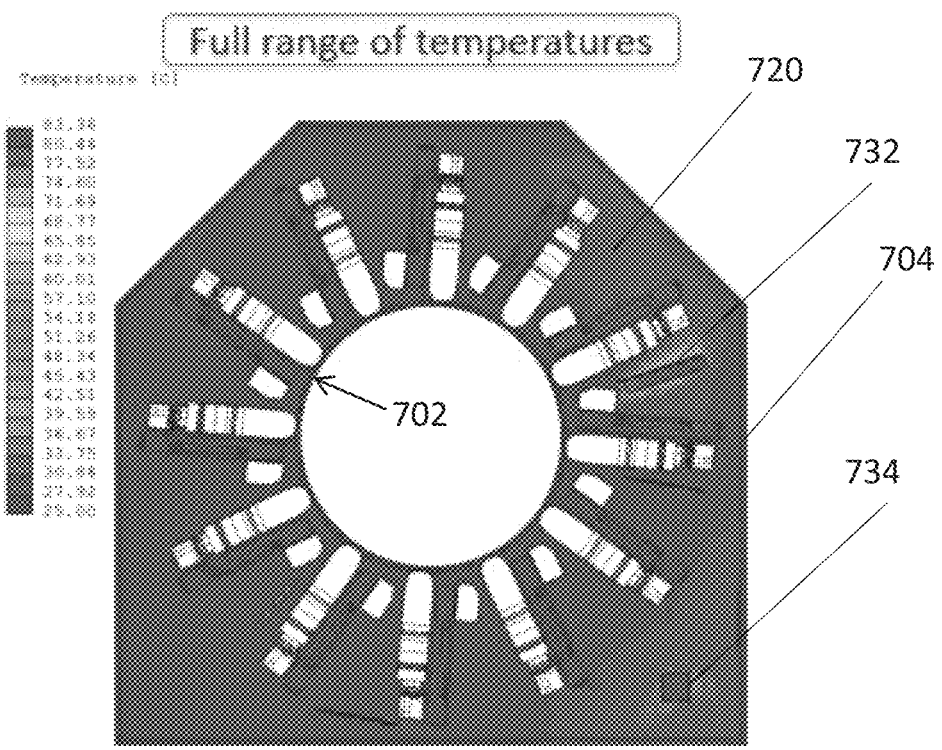
Figure 7B:
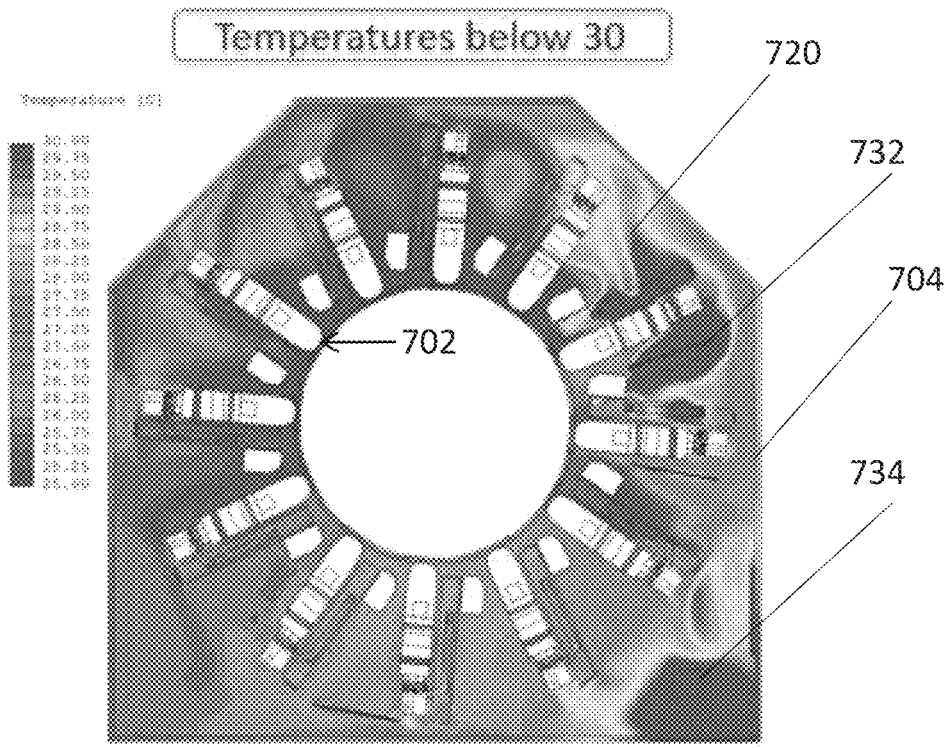
Figure 8:
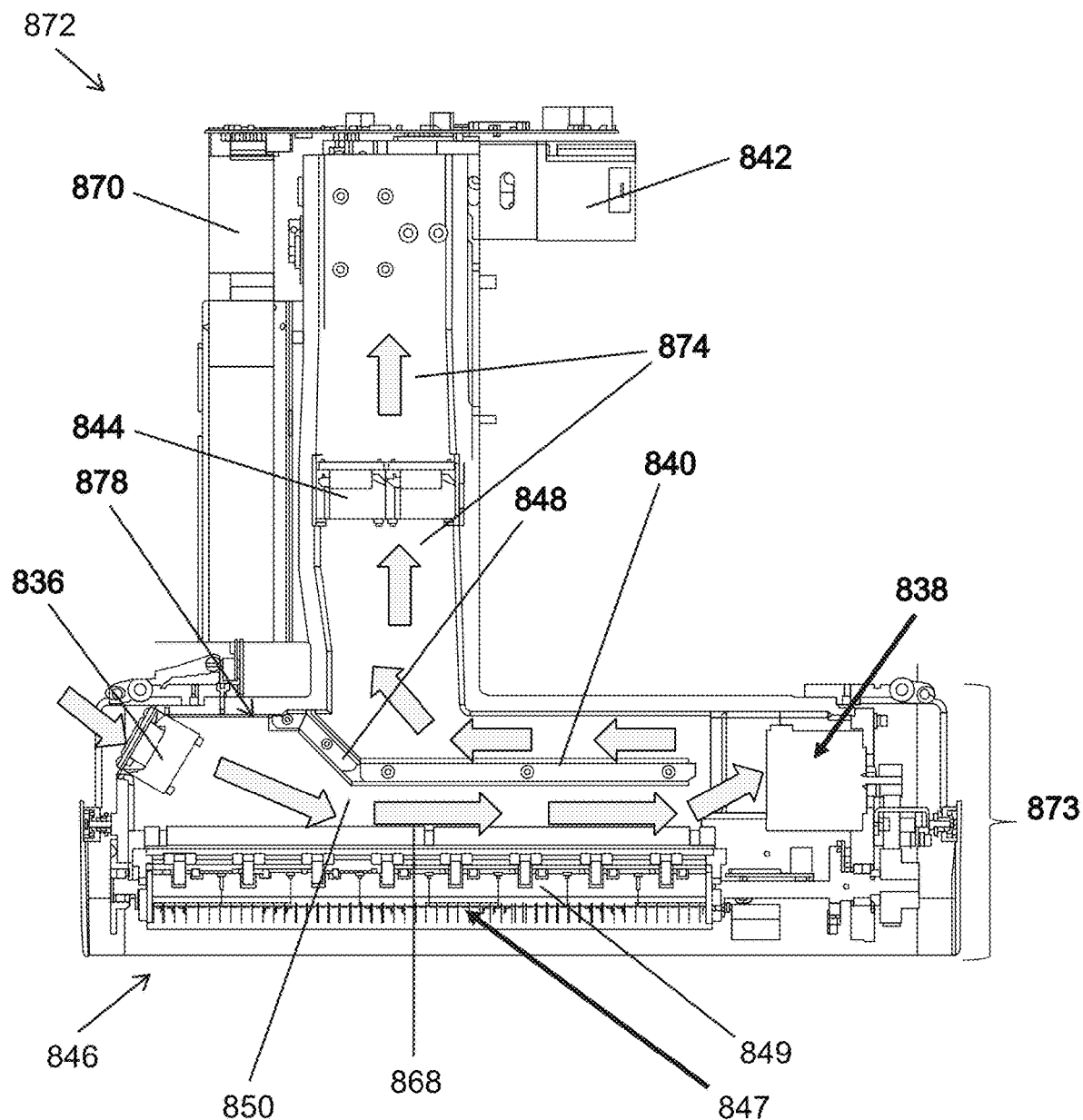
Figure 9:
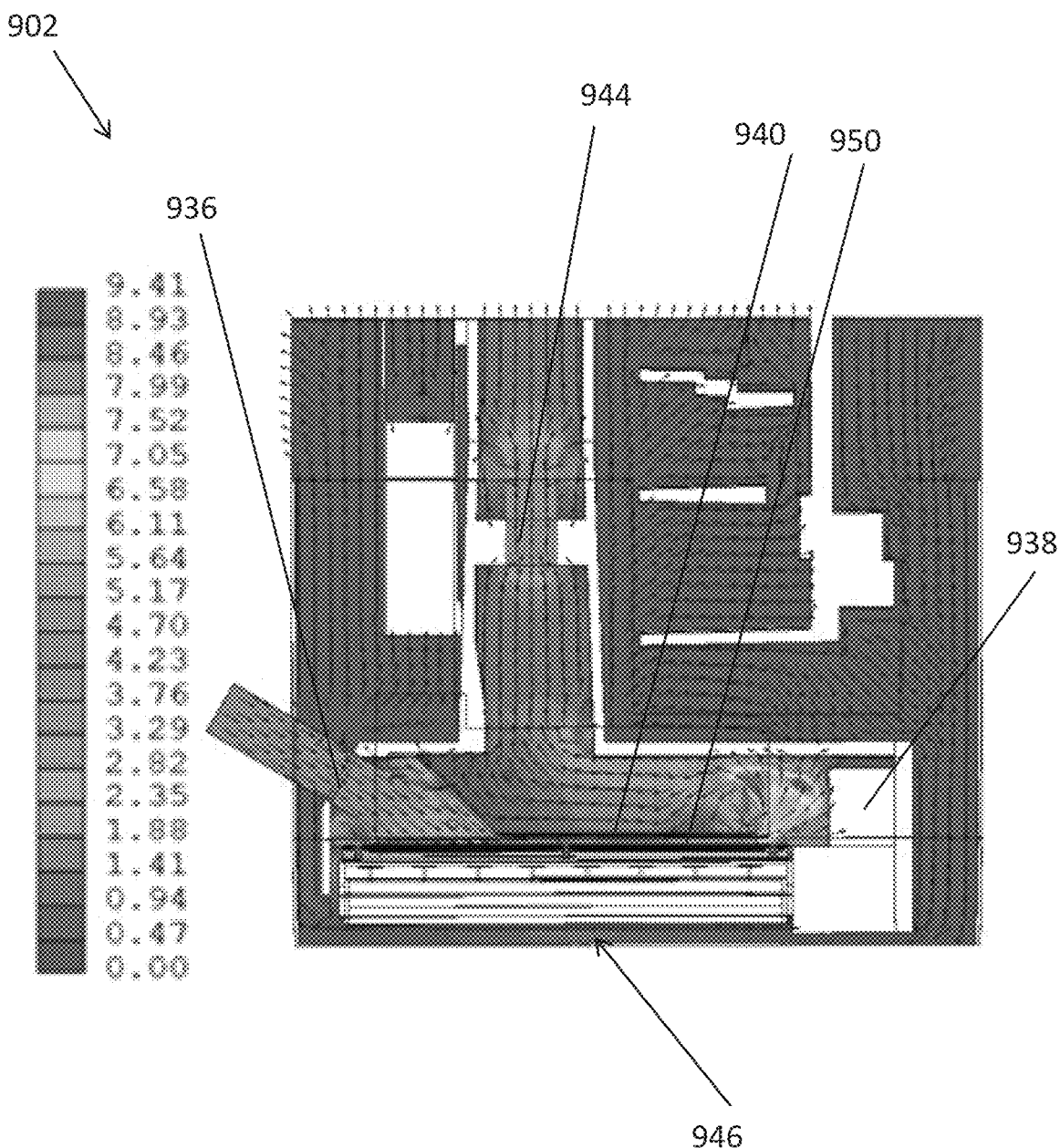
Figure 10:
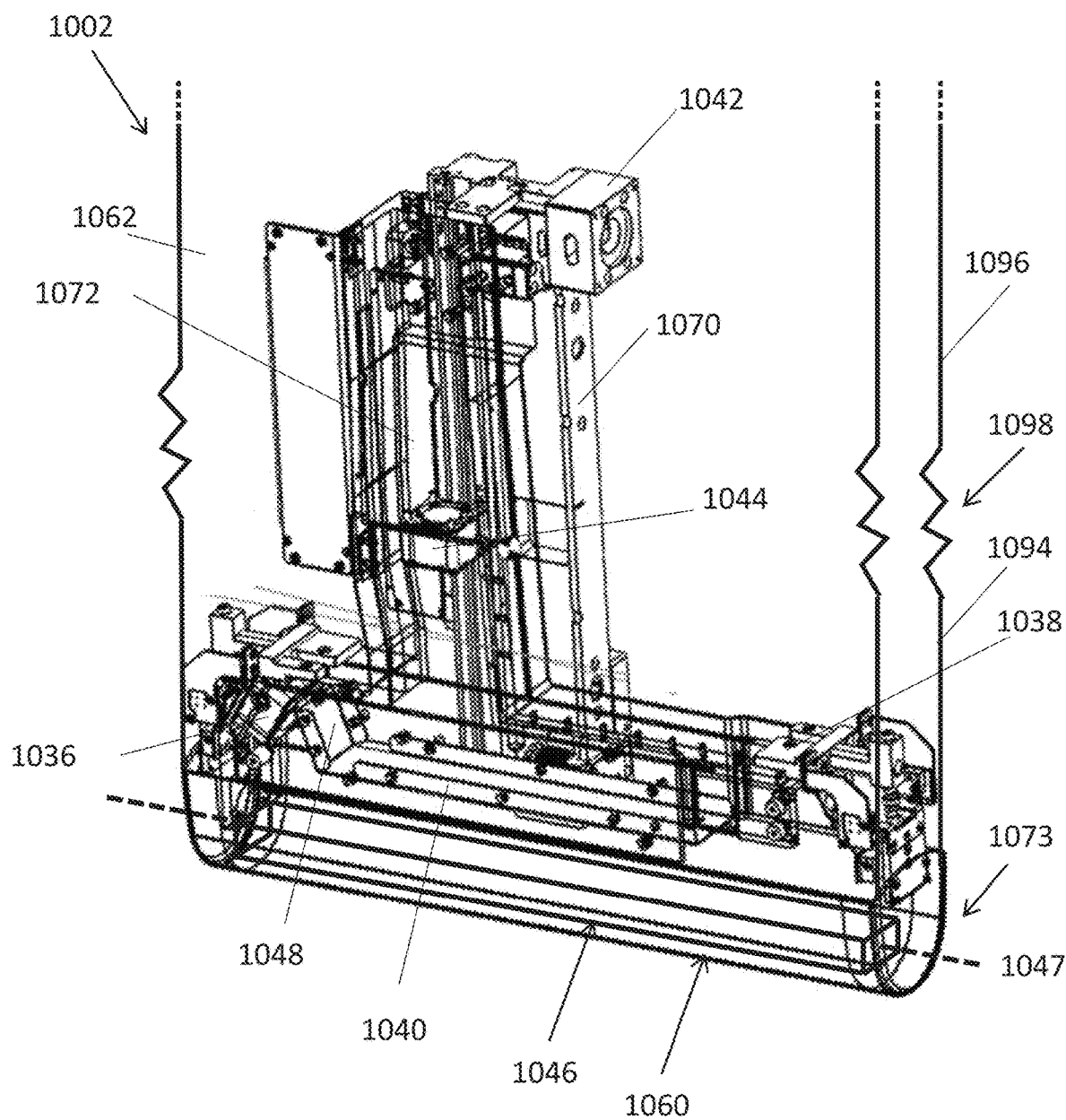
Figure 11:
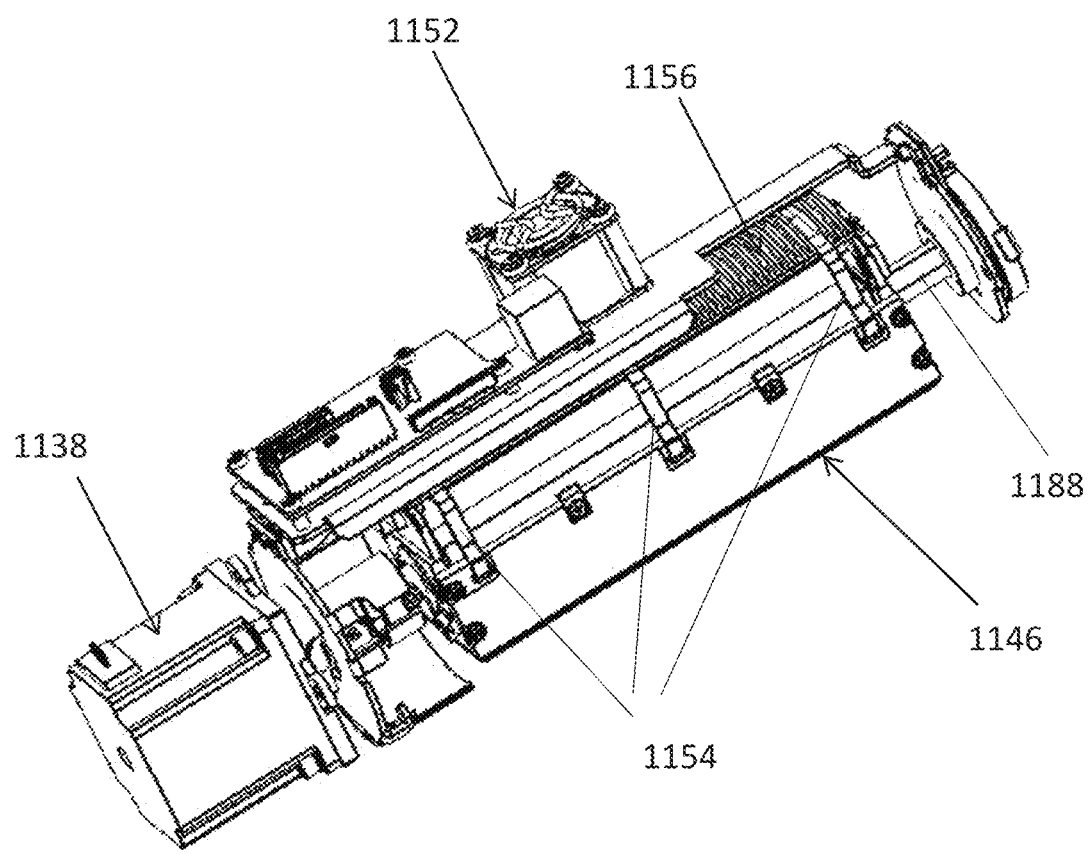
Figure 12:
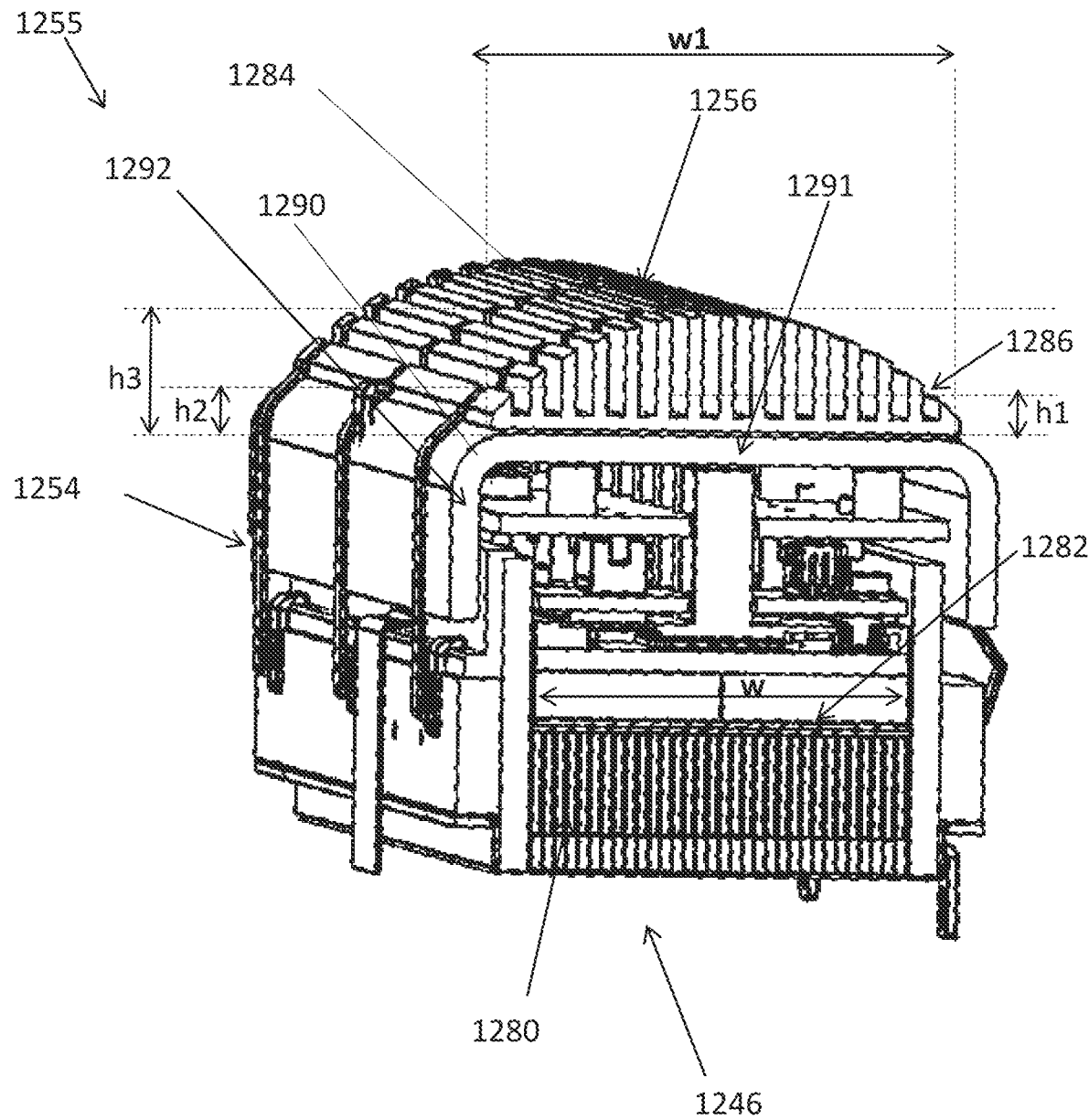
Figure 13A:
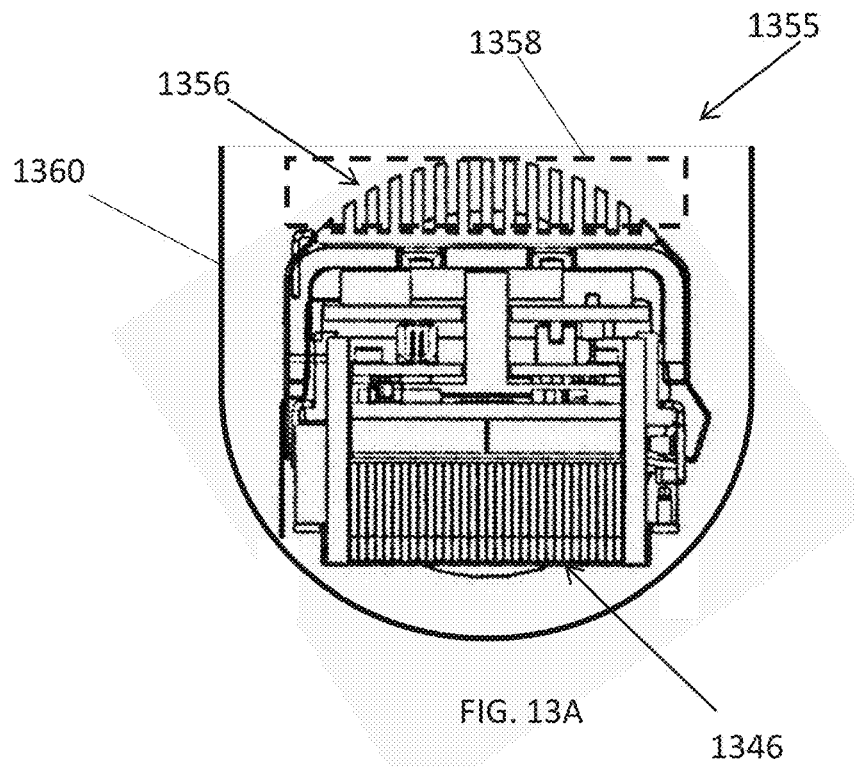
Figure 13B:
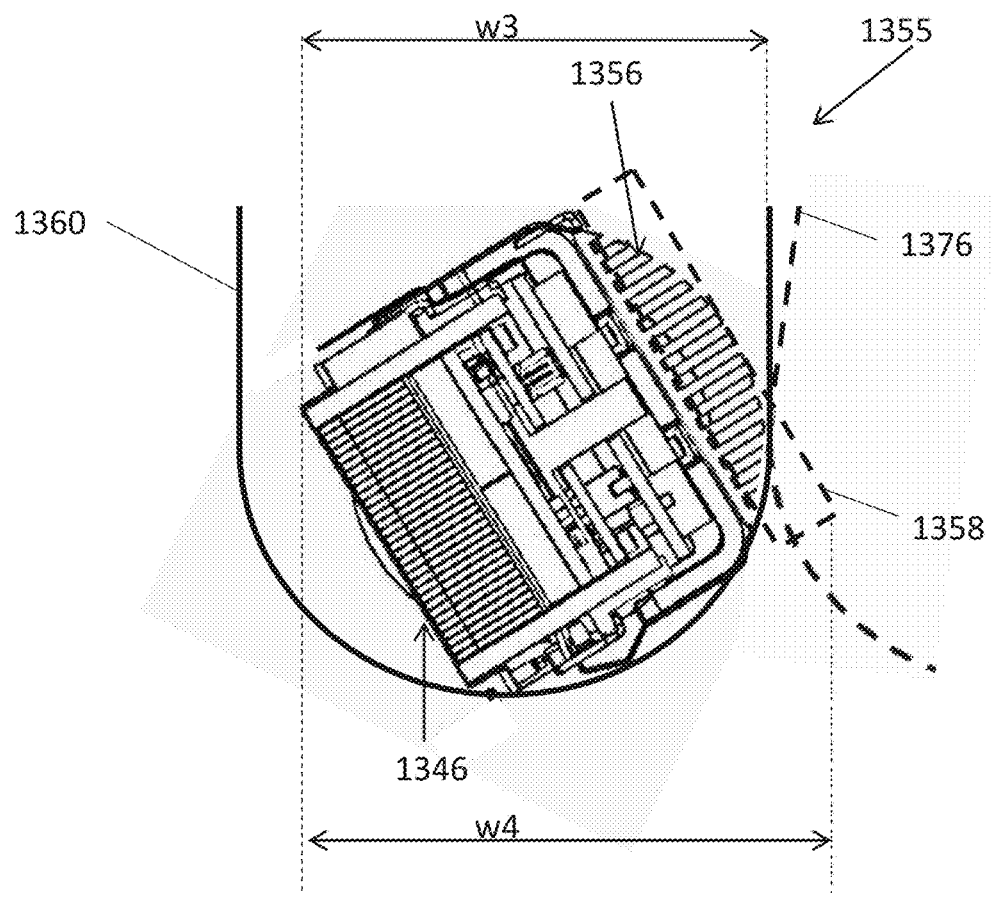
Figure 14A:
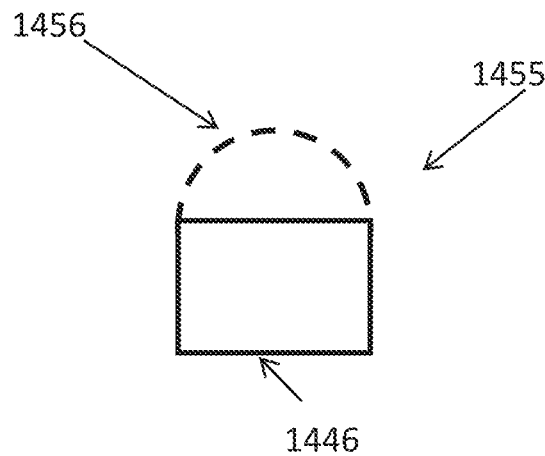
Figure 14B:
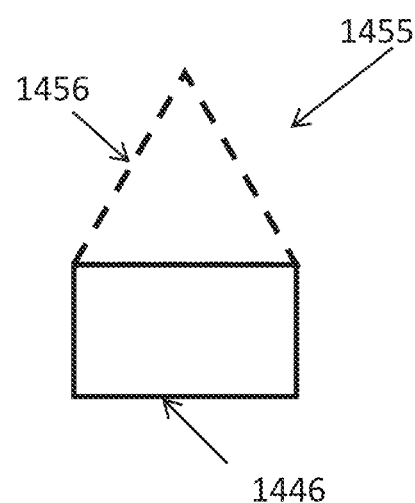
Figure 14C:
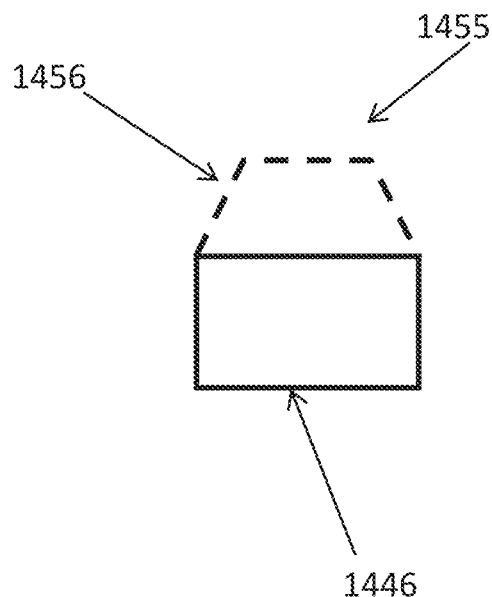

FIGS. 7A-B are simplified schematic cross sectional views of simulation results for temperature within a NMTS, during operation of the NMTS, according to some embodiments of the invention;

FIG. 8 is a simplified schematic sectional view of a detector unit, according to some embodiments of the invention;

FIG. 9 is a simplified schematic cross sectional view of simulation results for air velocity within a detector arm, according to some embodiments of the invention;

FIG. 10 is a simplified schematic view of a detector unit, according to some embodiments of the invention;

FIG. 11 is a simplified schematic view of inner portions of a detector head, according to some embodiments of the invention;

FIG. 12 is a simplified schematic of inner portions of a detector head including a shaped heat sink, according to some embodiments of the invention;

FIGS. 13A-B are simplified front views of portions of a detector camera unit within a detector cover, according to some embodiments of the invention; and FIGS. 14A-C are simplified schematic exemplary detector camera unit cross sections, according to some embodiments of the invention.

DESCRIPTION OF SPECIFIC EMBODIMENTS OF THE INVENTION

The present invention, in some embodiments thereof, relates to cooling of an imaging system and, more particularly, but not exclusively, to cooling of a nuclear medicine tomography system including a plurality of detector heads mounted on a detector carrier where the detector heads are translatable with respect to the detector carrier.

Overview

A broad aspect of some embodiments of the invention relates to cooling of an imaging system, for example, of a nuclear medicine tomography system (NMTS), where, in some embodiments, the system includes a plurality of detector units which are translatable with respect to a detector carrier on which the detector units are mounted (e.g. linearly translatable). In some embodiments, the NMTS is a SPECT (single-photon emission computed tomography) system. In some embodiments, the system is a PET, CT, MRI or a combination imaging system including more than one of SPECT, PET, CT, MRI, and ultrasound imaging e.g. a system including both SPECT and CT imagers.

In some embodiments, cooling is of detector cameras, where each detector unit includes a detector camera located within a distal portion of the detector unit. Where, in some embodiments, one or more detector camera is translatable (e.g. by extension of a portion of a detector unit housing the detector camera) into a bore of the NMTS. In some embodiments, cooling of the detector cameras is by transfer of heat from the detector cameras to inner space/s of a housing of the detector carrier.

In some embodiments, detector cameras are gamma detector cameras (e.g. for SPECT imaging). In some embodiments, each detector head includes a gamma detector camera.

In some embodiments, cooling reduces and/or maintains a temperature of detector cameras below a threshold and/or within a desired temperature range. In some embodiments, cooling is associated with transferring heat away from portions of the device involved in moving the detector heads, e.g. actuator/s e.g. actuators configured to translate detector head/s and/or rotate the detector carrier.

In some embodiments, cooling includes flow of air (and/or another fluid) past surface/s to be cooled (e.g. surface/s coupled to detector camera/s). In some embodiments, air flow is controlled by one or more fan.

In some embodiments, air is pulled into a detector unit from a distal end of the detector unit, e.g. adjacent to the detector camera for example, by one or more fan. In some embodiments, air is pulled into the detector unit from a bore of the imaging system where, for example, the distal end of detector unit/s is located within the bore. Where, in some embodiments, the bore is a space within the imaging system in which at least a portion of a patient is placed for scanning by the system (e.g. the patient rests on a bed, which is positioned within the bore). In some embodiments, the bore is a region of space into which the detector unit/s are extendable (and/or retractable). In some embodiments, the bore is a cylindrical space defined by a housing of the detector carrier. In some embodiments, air is pulled into the detector unit from air adjacent to the distal end of the detector unit, which is, in some embodiments within a detector unit cover.

In some embodiments, the flow of air exits the detector unit into an inner space of a housing of the detector carrier. In some embodiments, air within the inner space is cooled by one or more cooler, which, for example, includes one or more heat exchanger and/or evaporator and/or compressor. In some embodiments, the system lacks air flow into the bore from the system, for example, in some embodiments, there no is forced blowing of air (e.g. cool air) into the bore e.g. onto the patient.

An aspect of some embodiments of the invention relates to closed loop cooling of a NMTS where air flows in a closed loop through one or more part of the system. For example, here air within one or more part of the system is separated from air outside the system (e.g. outside housings of the system, e.g. the housings blocking mixing of system air with outside air).

In some embodiments, fluid (e.g. air) is circulated within a closed loop within one or more detector unit. For example where air circulating within the detector unit is cooled by one or more heat exchanger.

In some embodiments, fluid (e.g. air) flows through an inner space of a system housing (e.g. detector carrier housing) in a closed loop. In some embodiments, the system includes a heat pump configured to transfer heat out of fluid circulating through the closed loop. For example, in some embodiments, the closed loop includes a channel through one or more cooler configured to cool the air within the loop.

In some embodiments, air is circulated within a closed system housing and from the housing in and out of at least one detector unit, where, in some embodiments, the detector unit is separated from ambient air e.g. by a cover.

In some embodiments, air is drawn into a detector unit through a cooling channel and is exhausted out of the detector unit though an exhaust channel which terminates inside the inner space of the detector carrier housing. In some embodiments, the cooling channel is an area between a detector unit cover and other portions of the detector unit, cool air flowing from the inner space into a distal end of the detector unit. Where, in some embodiments, a detector camera is located at the distal end and/or the distal end extends into a bore space of the system.

In some embodiments, a temperature within the detector unit/s and/or detector carrier housing is maintained at a lower temperature than that of air outside the housing, for example, air temperature surrounding a patient being scanned by the tomography system. In some embodiments, air temperature within detector unit/s is selected and/or controlled to be below a threshold and/or within a range where, for example, the threshold and/or range is selected to reduce detector camera noise. In some embodiments, air temperature within a room housing the NMTS is selected for patient comfort. In some embodiments, the detector unit air temperature is lower than the ambient air temperature within the room in which the system is located.

An aspect of some embodiments of the invention relates to cooling of an imaging system (e.g. a NMTS) where temperature of air surrounding a patient is maintained at a temperature selected for patient comfort e.g. when the patient is undressed. In some embodiments, a temperature within the system, for example, within one or more detector head and/or one or more portion of a detector carrier housing is at a lower temperature than ambient air temperature e.g. within a room in which the imaging system is located. For example, including ambient air in a bore of the imaging system. In an exemplary embodiment, the detector camera/s are at a lower temperature than the imaging system bore (e.g. at least 5% lower or at least 10% lower or 5-50% lower, or lower or higher or intermediate ranges or percentages) at least during scanning.

In some embodiments, the room temperature is selected for patient comfort. In some embodiments, one or more temperature within the detector carrier housing e.g. a temperature of one or more (e.g. all of a plurality) of detector camera is selected for to reduce and/or minimize detector camera noise e.g. low noise measurements collected with the detector camera/s. In some embodiments, temperature of detector camera/s (and/or other portion/s within the detector carrier housing) are maintained below a threshold and/or within a desired range. In some embodiments, a system threshold temperature is below the desired room temperature range.

In some embodiments, a user (e.g. manually) selects a room temperature, e.g. at a user interface of a room cooler (e.g. AC system room control user interface).

In some embodiments, a system processor generates control signal/s for one or more temperature regulator, for example a cooler configured to cool air within the system housing and/or a temperature regulator configured to regulate temperature of ambient air within the room in which the system is housed. In some embodiments, the control signal/s are generated based on one or more sensor measurement e.g. temperature sensor measurement of a sensor which is, for example, configured to measure temperature at one or more point within the system housing.

In some embodiments, temperatures within the housing of the imaging system are controlled by a processor, which receives measurement data from imaging system sensor/s and generates control signal/s. In some embodiments, control signal/s control of one or more actuator.

For example, to control fan actuator/s e.g. to control temperature by changing flow of air through the system e.g. to control rate of heat exchange at a heat exchanger by changing flow of air through the heat exchanger. For example, to control pump actuator/s, e.g. to control air flow and/or other fluid flow (e.g. liquid flow through a heat exchanger). For example, to control compressor and/or evaporator actuator/s. For example, a control signal providing a waveform control signal to an inverter air conditioner compressor motor.

An aspect of some embodiments of the invention relates to an imaging system including a plurality of detector units, where each detector unit includes a detector camera and a detector unit cooling system. In some embodiments, the cooling system includes one or more channel through which fluid (e.g. air) is circulated. In some embodiments, the cooling system includes one or more fan positioned to circulate fluid e.g. through the channel/s.

In some embodiments, each detector unit includes at least one sensor configured to measure temperature of each detector camera. In some embodiments, temperature for each detector camera is controlled separately, for example, a control signal based on sensor measurement (e.g. for a detector camera) is sent to one or more actuator configured to cool the detector camera (e.g. fan actuator/s).

An aspect of some embodiments of the invention relates to a heat sink for a movable detector camera of an imaging system. In some embodiments, the system includes a plurality of detector units, each unit including one or more detector camera. In some embodiments, the system includes a controller which is configured to move a plurality of detector units where each detector unit includes a detector camera. In some embodiments, a movable detector camera unit (e.g. including a detector camera and a heat sink coupled to the detector camera) is configured to be moved into close proximity to one or more additional detector camera unit. In some embodiments, the movable detector camera unit is configured to be rotated (e.g. during acquisition of images) where rotation increases a proximity of a portion of the camera to another detector camera (and/or detector unit) of the system. In some embodiments, a detector camera unit includes a heat sink, which is shaped to have reduced volume in an area which is moved (e.g. rotated) into proximity with another detector camera unit. The reduced volume potentially decreasing a minimum distance required between the detector camera units to allow rotation of one or more of the detector units. The reduced volume potentially enables the controller to position the detector camera units in closer proximity.

In some embodiments, the detector unit includes a heat sink coupled to a detector camera. In some embodiments, the heat sink rotates with the detector camera. In some embodiments, the heat sink is sized and/or shaped to minimize a dimension of a cover of the detector unit and/or to minimize a minimum separation between two detector units each including oscillating cameras. For example, in some embodiments, the heat sink includes a shape (where, in some embodiments, the shape is an outer contour connecting a distal end of a plurality of fins) where one or more portion of the heat sink (e.g. heat sink outer contour) is thinner and/or extends a smaller distance from the detector camera than one or more other portion of the heat sink. In some embodiments, the portion which extends less distance reduces a dimension of the detector camera unit e.g. when it is rotated.

In some embodiments, the heat sink has a cross sectional shape with a central region extending from a base which is coupled to the detector camera, where the central region height is taller than one or both heights of edge regions surrounding the central region. In an exemplary embodiment, the heat sink has an arc shaped cross section, where the circle describing the contour of the arc is centered on the axis of rotation of the detector camera. Where the heat sink cross section is taken perpendicular to the axis of rotation of the detector camera.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Imaging System

Figure 1A:
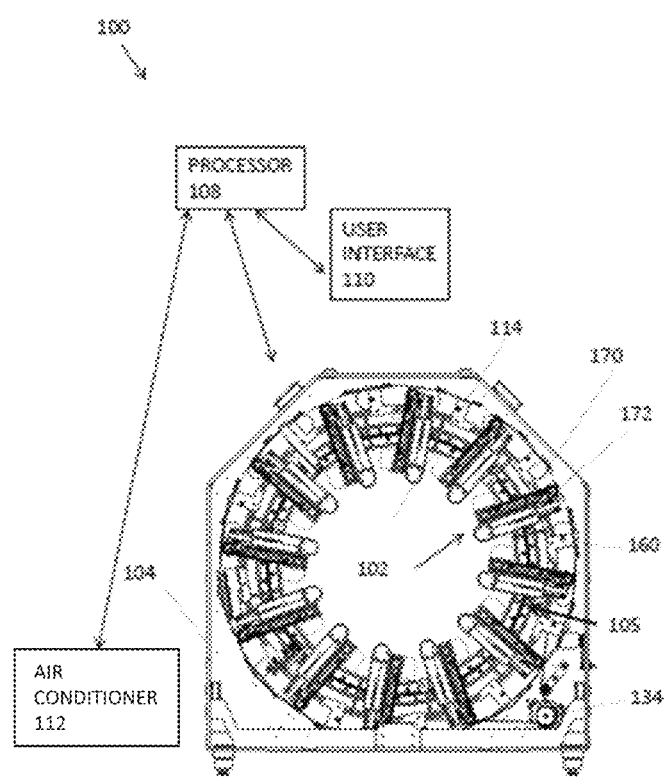
Figure 1B:
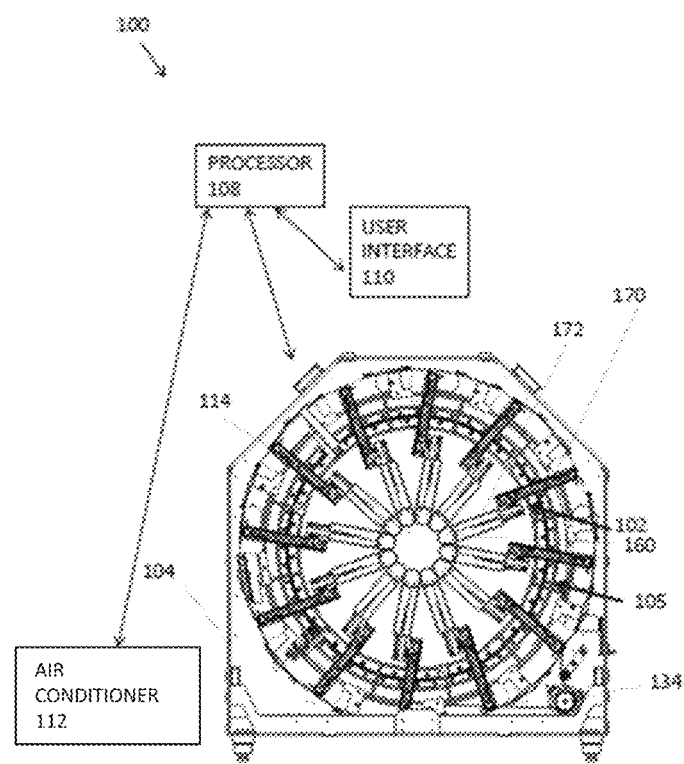

FIGS. 1A-B are simplified schematics of an imaging system 100, according to some embodiments of the invention. In some embodiments, the system is a nuclear medicine topography system (NMTS) e.g. a SPECT system.

In some embodiments, NMTS 100 includes a plurality of detector units 102 mounted to a detector carrier 105, which is coupled to a housing 104. In some embodiments, detector carrier 105 is rotatable within housing 104 where, rotation is, for example, actuated by a motor 134.

FIGS. 1A-B illustrate a side view of detector carrier 105 and detector units 102. In some embodiments, at least one, and in some embodiments, all detector units 102 include an extendable arm 172 on which a detector camera is mounted (e.g. within a cover 160), where the arm is movable with respect to detector carrier 105. In some embodiments, extendable arm 172 is coupled to a chassis 170, which is attached to the detector carrier (e.g. as described regarding FIGS. 1C-D).

In an exemplary embodiment, one or more detector unit 102 is linearly translatable with respect to detector carrier 105, e.g. towards and/or away from a center of the NMTS e.g. into and/or out of bore 114 of the NMTS. For example, in some embodiments, FIG. 1A illustrates all detector units 102 in a fully retracted configuration and FIG. 1B illustrates all detector units 102 in a fully advanced configuration.

In some embodiments, rotation of detector carrier 105 is about a center of a bore 114. In some embodiments, rotation is about an axis perpendicular to one or more axis of translation of the detector unit extendable arm/s. In some embodiments, rotation of detector carrier 105 rotates the detector units coupled to the detector carrier about the axis of detector carrier rotation.

In some embodiments, NMTS 100 includes a plurality of detector units 102, for example, 2-20, or 3-15, or 6-12, or lower or higher or intermediate ranges or numbers of detector units.

In some embodiments, at least a portion of a patient to be scanned is placed within bore 114 (e.g. the patient resting on a support e.g. a bed). Potentially, translation of detector unit/s enables detector camera/s within the unit/s to be in close contact (potentially improving accuracy of scanning) with a patient and/or a region of interest (ROI) of the patient and/or in close contact with other detector camera/s e.g. potentially reducing loss of emitted radiation through gaps between detector cameras. In some embodiments, detector cameras are translated different distances with respect to detector carrier 105 e.g. following a body contour of a patient.

In some embodiments, NMTS 100 includes one or more processor 108, for example, hosting circuitry configured to receive data from and/or send data to one or more of a user interface 110, one or more sensor (e.g. a sensor located within an air conditioning unit 112 e.g. one or more sensor configured to measure one or more condition within the system e.g. a temperature sensor). In some embodiments, processor 108 receives detector camera data and uses image reconstruction algorithm/s to generate images from the detector camera data.

In some embodiments, processor sends control signals to actuator/s within detector carrier 105 and/or within detector unit/s, based on signals received from one or more sensor and/or from user interface 110.

In some embodiments, user interface 110 includes a touch screen. Where, in some embodiments, a user controls the system e.g. by selecting system control options (e.g. scan type) and/or views system data (e.g. reconstructed image/s) on the touch screen.

In some embodiments, user interface 110 includes one or more audio control. In some embodiments, user interface 110 includes a microphone, where a sound signal generated by the microphone is received by processor 108, which includes circuitry configured to recognize user instructions from sound data. For example, where a user controls the system by audio commands, e.g. vocal commands.

In some embodiments, user interface includes one or more camera, where processor 108 receives camera data. In some embodiments, the processor includes circuitry configured for face recognition where, for example, in some embodiments, processor 108 accesses a memory (not illustrated) including a stored set of allowed user credentials, e.g. including data regarding facial feature/s. In some embodiments, the processor compares facial features extracted from camera images with the stored set of allowed user credentials and allows access and/or operation of one or more system feature when a match is identified.

Figure 1C:
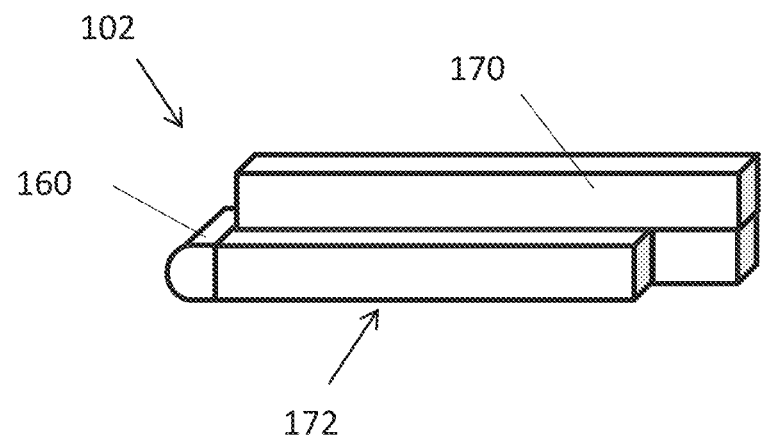
Figure 1D:
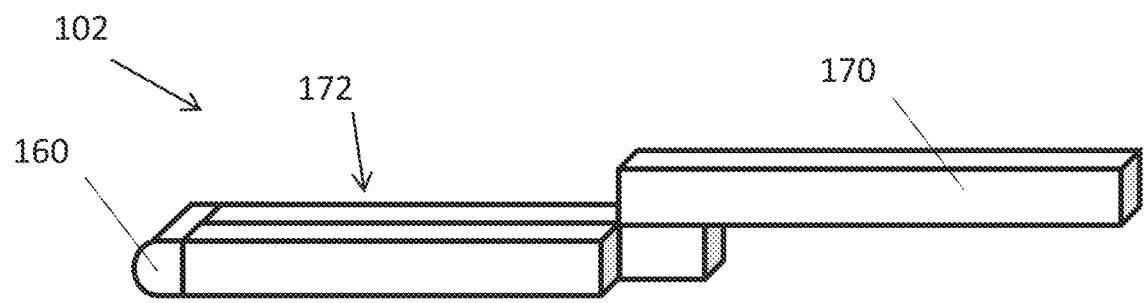

FIGS. 1C-D are simplified schematics of a detector unit 102, according to some embodiments of the invention. In some embodiments, detection unit 102 includes a stationary chassis 170 and an extendable arm 172, where extendable arm 172 is axially extendable from and along chassis 170. In some embodiments, chassis 170 is coupled to a detector carrier (e.g. 105 FIGS. 1A-B). In some embodiments, one or more actuator (not illustrated), for example, upon receiving a control signal (e.g. from a processor e.g. processor 108 FIGS. 1A-B) drives extendable arm 172 axially along stationary chassis 170 between a fully retracted position e.g. as illustrated in FIG. 1C and a fully extended position e.g. as illustrated in FIG. 1D.

Exemplary Cooling

FIG. 2A is a simplified schematic of air flow within an imaging system 200, according to some embodiments of the invention. Where, in some embodiments, imaging system 200 is an NMTS.

In some embodiments, NMTS 200 includes a plurality of movable detector units 202 (e.g. including one or more feature as described and/or illustrated regarding detector units 102 FIGS. 1A-D) mounted on a detector carrier 205.

In FIG. 2A direction of fluid flow (e.g. air flow) at one or more point is illustrated by arrows. In some embodiments, ambient air is circulated within detector units 202 and/or inner space 220 of a NMTS housing 204.

Optionally, in some embodiments, ambient air is cooled by a temperature regulator 212. For example, in some embodiments, temperature regulator 212 is a device configured to cool air within a room in which the NMTS is located. For example, an air conditioner (and/or other type of room cooler) dedicated to the room. For example, a central air conditioner providing cooling to more than one room, where, in some embodiments, an outlet of the central air conditioner opens into the room in which the NMTS is located. In some embodiments, temperature regulator 212 is configured to cool and/or heat e.g. air circulated through the temperature regulator.

In some embodiments, the system includes more than one cooler.

Optionally, in some embodiments, a cooler 213 is located within housing. For example, in some embodiments, cooler 213 includes a heat exchanger located within housing 204 where, in some embodiments, the heat exchanger is a radiator, where, for example, air is cooled by flows over one or more pipe through which a fluid (e.g. water) is circulated. In some embodiments, one or more heat exchanger is cooled using a liquid, which is gas at room temperature and atmospheric pressure e.g. liquid nitrogen.

In some embodiments, a first portion of a cooler is located within housing 204 and a second portion of cooler is connected to the first portion and is located outside the housing. For example, in some embodiments, heat exchanger 213 is a radiator located within the housing and fluid circulating within the radiator is cooled by component/s outside the housing (not illustrated), e.g. a compressor and/or an evaporator configured to cool the radiator fluid.

In some embodiments, a detector unit (e.g. more than one, e.g. each detector unit) includes and/or is thermally coupled to a separate cooler. In some embodiments, a detector unit (e.g. more than one, e.g. each detector unit) includes a heat exchanger.

In some embodiments, air circulation within NMTS 200 includes flow of air into inner space 220, for example, through one or more inlet/s 206 where, in some embodiments, inlet/s 206 are located in a base portion of housing 204. In some embodiments, air flows generally upwards within inner space 220 and exits the housing through one or more outlet 207, where in some embodiments, outlet/s 207 are located in an upper portion of the housing.

In some embodiments, air flows into one or more detector unit 202 from a bore 214. In some embodiments, air flows through the detector unit/s into inner space 220, then, in some embodiments, flowing through inner space 220 in an upwards direction towards outlets 207. In some embodiments, the detector carrier is centered around a center of the bore.

In some embodiments, NMTS 200 includes one or more feature e.g. as described with reference to FIGS. 5-10. In some embodiments, air flow within NMTS 200 is directed by one or more fan, e.g. according to the air flow paths illustrated by arrows. Alternatively or additionally, in some embodiments, one or more pump 217 directs air flow.

In some embodiments, air flow is directed past a heat sink mounted on one or more portion of the system, e.g. coupled to a detector camera (including one or more feature described regarding and/or illustrated by e.g. heat sinks 1256 FIG. 12, 1356 FIGS. 13A-B). In some embodiments, a collimator of a detector camera (e.g. collimator 1280 FIG. 12) acts as heat sink, for example, where, in some embodiments, air is circulated past the collimator (e.g. by a fan) for example, collimator septa forming heat transfer surfaces.

In some embodiments, air from within the housing and/or detector unit/s is exhausted into the bore. For example, air heated by the system is used to heat a space in which a patient being scanned is located, e.g. the heating potentially increasing patient comfort.

In some embodiments, NMTS 200 includes one or more sensor 299. In some embodiments, sensor 299 is a temperature sensor, which, for example, generates a signal based on a temperature within one or more point within the system, for example, within housing 204 and/or within one or more detector unit 202. In some embodiments, each detector unit includes a sensor which is, for example, configured to measure a temperature of a portion of the detector unit e.g. of a detector camera and/or from which can be inferred a temperature of the detector camera. Alternatively or additionally, one or more sensor is configured to sense air flow speed within one more portion of housing 204 and/or detector unit 202.

In some embodiments, one or more sensor, e.g. sensor 299 sends data to a processor 208. In some embodiments, processor sends a control signal to one or more cooler, e.g. cooler 212, 213, e.g. based on received sensor signal/s. For example, in some embodiments, sensor 299 signal is used to generate a thermostat control signal for cooler 212.

Figure 2B:
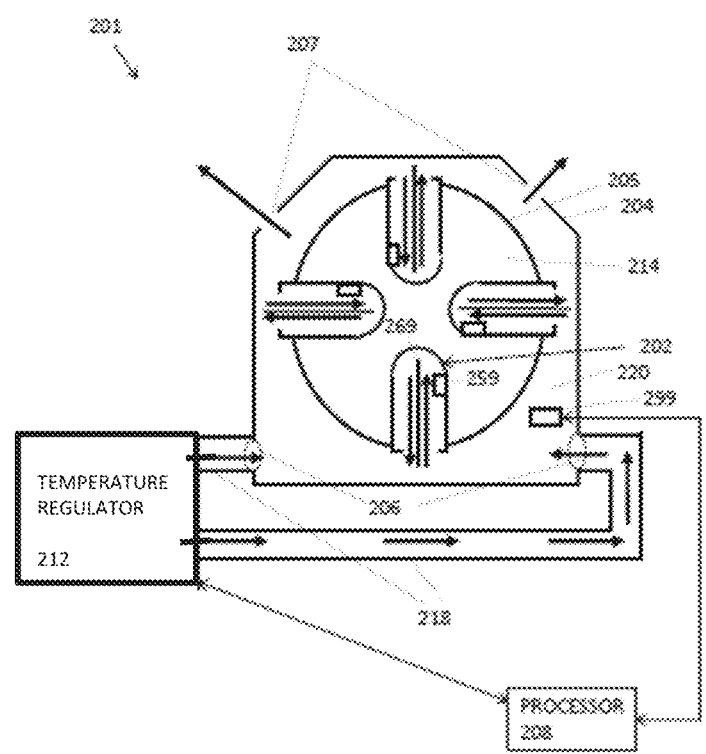
FIG. 2B is a simplified schematic of air flow within an imaging system, according to some embodiments of the invention.

FIG. 2B is a simplified schematic of air flow within an imaging system 201, according to some embodiments of the invention.

Figure 4A:
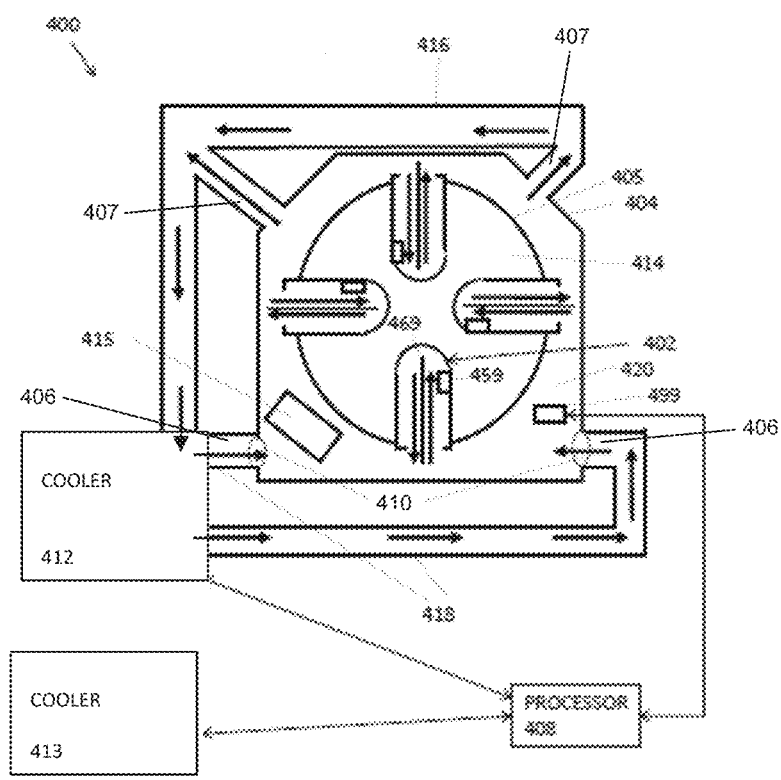
FIG. 4A is a simplified schematic of an imaging system with closed loop cooling, according to some embodiments of the invention.
Figure 4B:
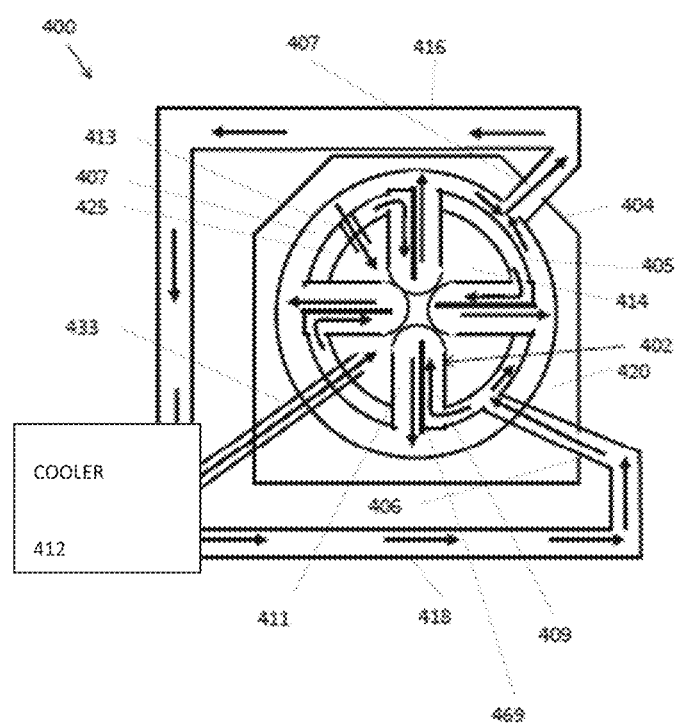
FIG. 4B is a simplified schematic of an imaging system with closed loop cooling, according to some embodiments of the invention.
Figure 4C:
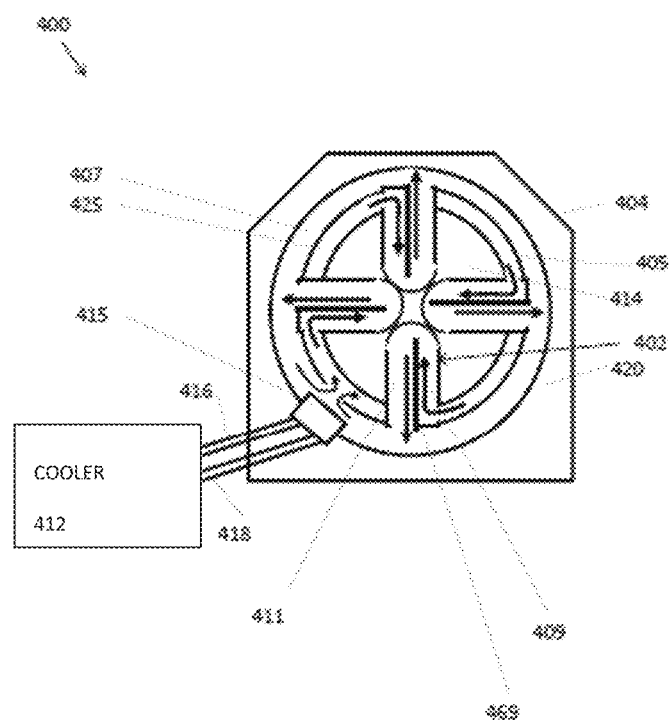
FIG. 4C is a simplified schematic of a n imaging system with closed loop cooling, according to some embodiments of the invention.

In some embodiments, system 200 includes one or more feature as described and/or illustrated regarding system 200 FIG. 2A and/or system 400 FIGS. 4A-C In some embodiments, a cooler 212 is connected to one or more inlet (e.g. inlets 206) in a housing 204, for example, by one or more channel 218, for example, transferring cooled air into housing 204 through the channel/s into the inlet/s. In some embodiments, warm air diffused out of the system through outlet/s 207.

In some embodiments, cool air within housing 204 is circulated within detector units 202, e.g. as described regarding detector units 404 FIG. 4A.

Exemplary Method of Cooling

Figure 3A:
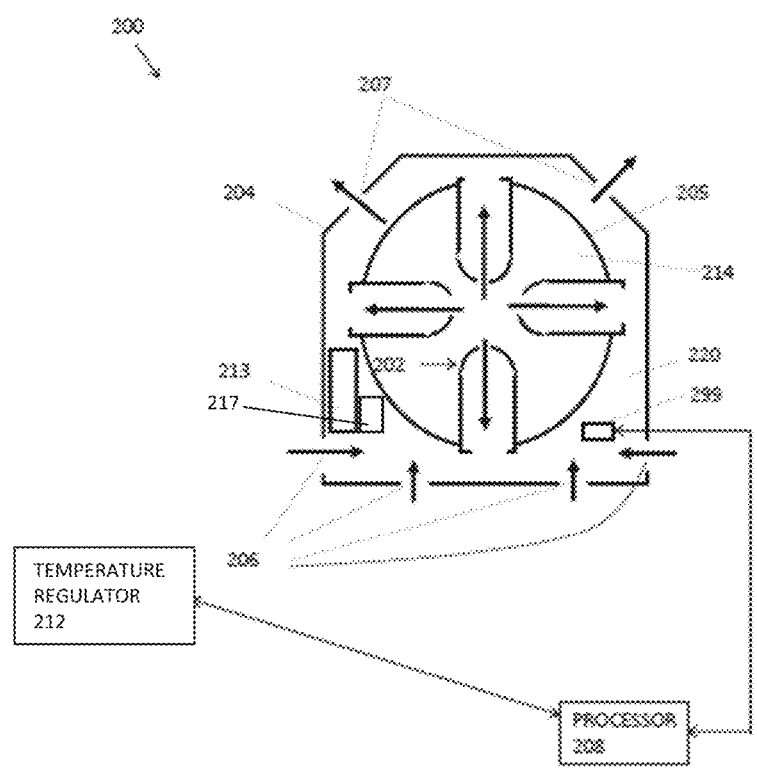
FIG. 3A is a flow chart of a method of cooling an imaging system, according to some embodiments of the invention.

FIG. 3A is a flow chart of a method of cooling an imaging system, according to some embodiments of the invention. In some embodiments, the imaging system is an NMTS.

At 300, in some embodiments, temperature at one or more point within an imaging system (e.g. a NMTS) is measured e.g. by a sensor (e.g. sensor 299 FIG. 2A, sensor 499 FIG. 4A).

At 302, in some embodiments, cooling of one or more portion of the system is adjusted, based on the temperature measurement/s.

In some embodiments, a processor (e.g. including one or more feature described and/or illustrated regarding processor 108 FIGS. 1A-B and/or processor 208 FIG. 2A and/or processor 408 FIG. 4A) receives sensor data and, based on the temperature and/or location of the temperature measurement, generates a control signal to change a temperature of one or more portion of the imaging system. In some embodiments, a control signal is based on measurement from a single sensor. Alternatively, in some embodiments, a control signal is based on more than one sensor measurement. In some embodiments, the processor sends the control signal to one or more actuator e.g. to control fluid flow.

In some embodiments, cooling is adjusted by changing fluid flow in one or more region of the imaging system.

In some embodiments, control of fluid flow includes control of volumetric fluid flow rate past a surface to be cooled e.g. air flow past portion/s of the imaging system. In some embodiments, control is of fluid flow past a heat exchanger e.g. to change a rate of temperature change of the fluid e.g. to cool the fluid faster. In some embodiments, control is of fluid flow within a heat exchanger (e.g. flow of coolant fluid within pipes of a radiator heat exchange). In some embodiments, control is of fluid flow to one or more evaporator e.g. from one or more compressor. Where flow, in some embodiments, refers to volumetric flow rate. In some embodiments, an actuator receiving the control signal is for example, a fan actuator, a pump actuator, a motor actuator. In some embodiments, control signal/s instruct one or more compressor motor.

In some embodiments, the control signal instructs activation and/or deactivation and/or operation of one or more actuator (e.g. speed of fan rotation, pump speed and/or strength, compressor motor speed and/or power) is controlled when temperature rises above and/or falls below a desired temperature range.

In some embodiments, the processor generates and/or sends a control signal to one or more actuator to change operation of the actuator when one or more measured temperature passes and/or approaches a threshold and/or falls outside an allowable range and/or approaches a limit to an allowable range.

In some embodiments, the processor receives a measurement signal from one or more sensor located outside the system, for example, one or more sensor mounted on a detector carrier housing configured to measure temperature outside the housing. For example, one or more sensor configured to measure conditions (e.g. temperature) in a room in which the imaging system is located. For example, one or more sensor configured to measure temperature within a bore of the system.

In some embodiments, sensor data regarding condition/s outside the system is received by the processor, and in some embodiments, one or more control signal (e.g. as described above) is generated based on the data. For example, in some embodiments, cooling of and/or within one or more portion of the system is adjusted based on measured temperature outside the housing of the imaging system and/or a temperature differential between temperature outside the housing and temperature within the housing.

In some embodiments, based on temperature measurements and/or data regarding cooling potential of system cooler/s a processor estimates ability of the system to maintain temperature of one or more part of the system e.g. within a desired temperature range, e.g. below a threshold temperature. In some embodiments, an alert signal is generated when it is estimated that the range will be breached and/or the threshold temperature is exceeded. In some embodiments, upon generation of an alert signal, a warning and/or alarm is communicated to a user through a system user interface. In some embodiments, upon generation of an alert signal, imaging with the system is disabled.

In some embodiments, cooling is reduced to one or more detector unit. For example, when one or more of the plurality of detector units is non-operative and/or not used for imaging (e.g. when imaging a small region, in some embodiments, a subset of the plurality of detector heads are advanced and/or used for scanning). In some embodiments, the processor, based on data concerning which detector units are in use, sends one or more control signal, e.g. to one or more actuator and/or as described above.

In some embodiments, measurement data received by the processor is used in reconstruction of images, for example, temperature data being used in a reconstruction algorithm, e.g. to compensate for temperature differences within a detector camera and/or between different detector cameras and/or to compensate for temperature being outside an allowed and/or desired range.

In some embodiments, a control signal is generated for each detector unit. Where, for example, in some embodiments, a control signal is generated for each detector unit based on sensor data from sensor/s of the detector unit. Alternatively or additionally, in some embodiments, a control signal is generated for one or more detector unit based on sensor data from one or more of the detector unit, other detector unit/s, other system sensor/s (e.g. sensor/s located within the housing).

In some embodiments, a desired system temperature range has a lower threshold and an upper threshold. In some embodiments, different portions of the system have different desired temperatures e.g. temperature ranges. In some embodiments, the desired temperature range for detector cameras is 15-30° C., or 17-25° C., or 18-24° C., or 18-25° C. or under 30° C. or under 25° C. or under 24° C. or lower or higher or intermediate temperatures or ranges. In some embodiments, the desired temperature range for detector cameras is associated with the material of the detector array e.g. material of scintillation crystal/s.

In some embodiments, one or more sensor is located in a detector unit and a processor (e.g. a detector unit processor and/or a system processor) generates control instructions for operation of one or more detector unit actuator, for example, fan motor/s (e.g. controlling fan speed), based on the sensor data. Where, for example, in some embodiments, the sensor data includes measured temperature and/or location of the sensor.

Figure 3A:
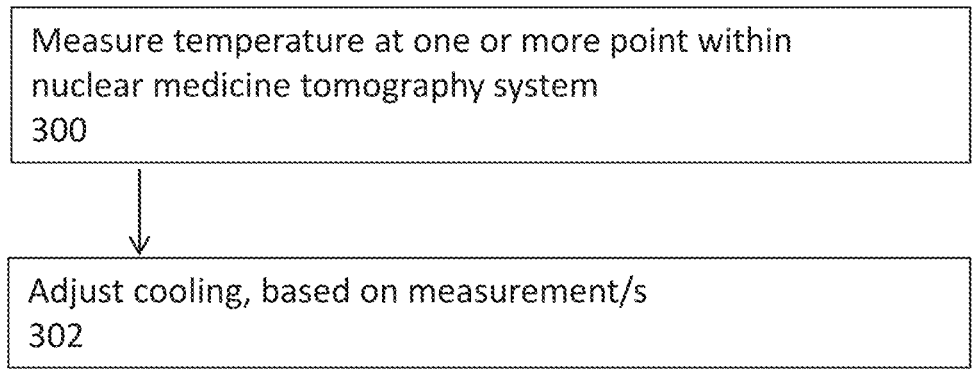
Figure 3B:
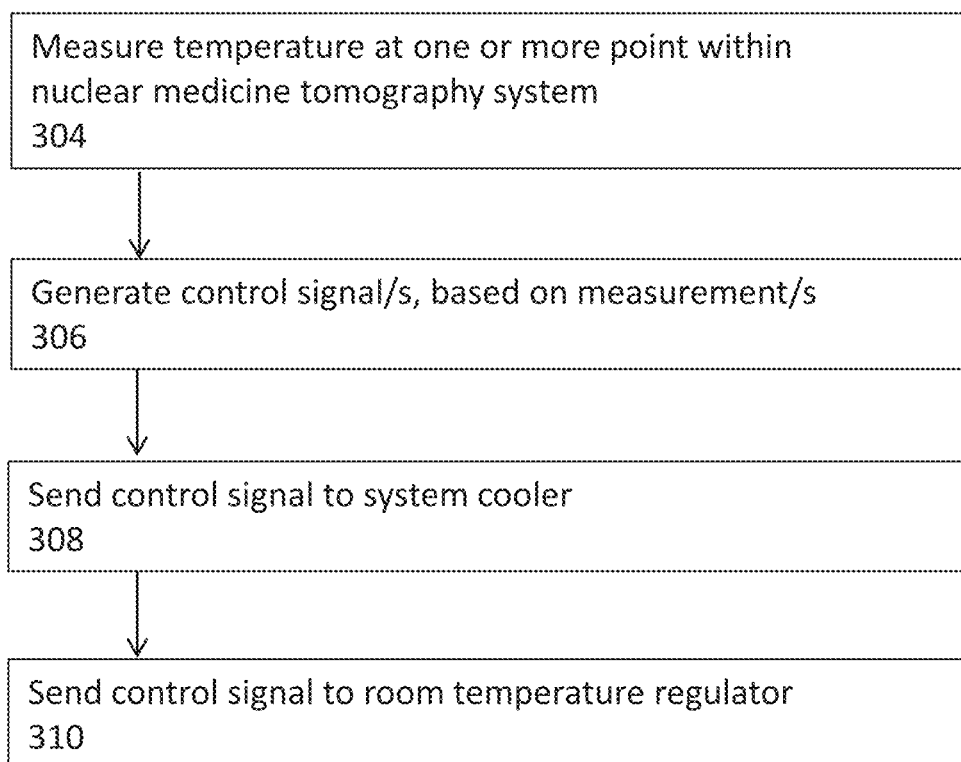
FIG. 3B is a flow chart of a method of temperature regulation for an imaging system, according to some embodiments of the invention.

FIG. 3B is a flow chart of a method of temperature regulation for an imaging system, according to some embodiments of the invention. In some embodiments, the imaging system is an NMTS.

At 304, in some embodiments, temperature is measured at one or more point within a NMTS e.g. by a sensor (e.g. sensor 299 FIG. 2A, sensor 499 FIGS. 4A-C, one or more sensor located configured to measure temperature within one or more detector unit). In some embodiments, one or more sensor measures one or more other parameter, e.g. air flow speed.

In some embodiments, temperature is measured within each detector unit, e.g. by at least one sensor configured to measure temperature (e.g. located within) each detector unit.

At 306, in some embodiments, one or more control signal is generated, based on the sensor measurements, e.g. by a processor (e.g. processor 208 FIG. 2A, 408 FIG. 4A) which, for example, receives sensor signal data.

At 308, in some embodiments, generated control signal/s are sent to a system cooler and/or temperature regulator and/or heat exchanger (e.g. 212, 213 FIG. 2A, 412, 413, 415 FIG. 4A). In some embodiments, control signal/s instruct one or more actuator e.g. as described regarding step 302 FIG. 3A.

At 310, in some embodiments, generated control signal/s are sent to a room temperature regulator (e.g. element 413 FIG. 4A) where, the control signal instructs operation of one or more actuator e.g. as described regarding step 302 FIG. 3A.

Exemplary Closed Loop Cooling

FIG. 4A is a simplified schematic of an imaging system 400 with closed loop cooling, according to some embodiments of the invention. Where, in some embodiments, imaging system 400 is an NMTS. In FIG. 4A direction of fluid flow (e.g. air flow) at one or more point is illustrated by arrows.

In some embodiments, NMTS 400 includes a plurality of movable detector units 402 (e.g. including one or more feature as described and/or illustrated regarding detector units 102 FIGS. 1A-D) mounted on a detector carrier 405.

In some embodiments, air (e.g. cooled air) flows from a cooler 412, through one or more input channel 418 and into an inner space 420 of a NMTS housing 404, for example, through one or more inlet 406, where, in some embodiments, inlet/s 406 are located in a base portion of the housing. In some embodiments, air flow is controlled at one or more of the inlets 406 by one or more fans (oval shapes 410 in some embodiments, each representing a fan).

In some embodiments, fluid (e.g. air) is treated before being inserted into the system, for example, is filtered (e.g. to remove dust) and/or dehumidified. For example, in some embodiments, air drawn into cooler 412 is treated (e.g. filtered) by the cooler. For example, in some embodiments, air entering housing 404 is treated, e.g. oval shapes 410 in some embodiments, additionally or alternatively representing filters and/or dehumidifiers.

In some embodiments, air within inner space 420 flows in a generally upwards direction towards one or more outlet 407, where, in some embodiments, outlet/s 407 are located in an upper portion of the housing. In some embodiments, air flow is controlled at one or more of the outlets 407 by one or more fans (circular shapes 430 in some embodiments, each representing a fan). In some embodiments, air exiting through outlet/s 407 returns to cooler 412 through one or more outlet channel 416.

In some embodiments, one or more detector unit 402 (e.g. each detector unit) is thermally insulated, e.g. potentially reducing heating of the detector unit (e.g. detector camera) by ambient air. In some embodiments, at least a portion of a detector camera and/or unit includes a layer of thermal insulation. In some embodiments, a detector unit includes a thermally insulating cover.

In some embodiments, one or more portion of housing 404 is thermally insulated. For example, reducing heating of the housing and/or air within the housing by air outside the housing (which, in some embodiments, is warmer). In some embodiments, housing 404 includes (e.g. one or more portion of the housing is covered by) a layer of thermal insulation.

In some embodiments, air flows from housing 404 into detector unit 402, flows past a detector camera and/or one or more heat generating portion of the detector unit (e.g. motor configured to rotate the camera e.g. as described elsewhere in this document). In some embodiments, the air then returns to housing 404. In some embodiments, a channel through which the air flows from housing 402 into detector unit 402 is separated by a separator 469 from a channel through which air flows back to the housing. In some embodiments, air flow for each of the plurality of detector units is as described regarding detector unit 402.

In some embodiments, air circulation within the NMTS e.g. within the housing, detector units, inlet and outlet pipes is separated from ambient air e.g. within a bore 414 and/or room housing the NMTS. Potentially, lack of mixing of ambient air with air circulating within the system prevents entrance and/or build-up of dirt and/or dust (e.g. airborne) within the NMTS, potentially reducing associated maintenance requirements. Potentially, the separation prevents entrance of radioactive tracers, for example, airborne tracers, e.g. when a patient inhales and exhales tracer/s during scanning.

In some embodiments, cooler 412 is an air conditioner e.g. an inverter air conditioner. In some embodiments, cooler 412 is a heat exchanger, e.g. a radiator fluid (e.g. air) flows over one or more pipe through which a fluid (e.g. a cooled fluid, e.g. water) is circulated. In some embodiments, the system includes more than one cooler. In some embodiments, an additional cooler 413 is located with a room in which the NMTS is located. In some embodiments, cooler 413 is an air conditioner. In some embodiments, cooler 413 controls ambient air temperature within a room in which the NMTS is located.

In some embodiments, at least a portion of a cooler 415 is located within housing 404. For example, cooler 415 having one or more feature as described and/or illustrated regarding cooler 213 FIG. 2A.

In some embodiments, NMTS 400 includes one or more sensor 499. In some embodiments, sensor 499 is a temperature sensor, which, for example, generates a signal based on a temperature within one or more point within the system, for example, within housing 404 and/or within one or more detector unit 402. In some embodiments, NMTS includes one or more sensor configured to measure a temperature outside of the housing. For example, a temperature of air within a room in which the NMTS is located. For example, a temperature of air within bore 414.

In some embodiments, a detector unit 402 includes a sensor 459, e.g. each detector unit includes at least one sensor. In some embodiments, a detector unit sensor 459 is configured to measure a temperature of a portion of the detector unit e.g. of a detector camera and/or a temperature from a detector unit portion from which the temperature of the detector camera can be estimated e.g. by a processor (e.g. processor 408). In some embodiments, a detector camera (e.g. each detector camera) includes a plurality of temperature sensors, located and/or measuring temperature at different parts of the detector camera.

Alternatively or additionally, one or more sensor is configured to sense fluid (e.g. air) flow speed within one more portion of housing 404 and/or detector unit/s 402 where, in some embodiments, fluid volumetric flow rate is estimated from air speed e.g. by a processor (e.g. processor 408).

In some embodiments, one or more sensor, e.g. sensor 499 sends sensor signal data to a processor 408. In some embodiments, processor generates control signal/s and/or sends control signal/s to one or both coolers 412, 413, e.g. based on received sensor signal/s. In some embodiments, control signal/s instruct one or more actuator e.g. as described regarding step 302 FIG. 3A, for example, to effect a change in temperature and/or to maintain a temperature. For example, in embodiments where cooler 412 is a radiator heat exchanger, in some embodiments, a control signal controls speed of flow of fluid (e.g. water) through the radiator pipes and/or air speed (e.g. actuated by one or more fan) past the pipes.

In some embodiments, a desired temperature for air within the room in which the NMTS is located and/or air with a NMTS bore, for example, for patient comfort, is about 20-30° C., or 25-30° C., or 24-26° C. or 23-36° C. In some embodiments, a desired temperature and/or temperature range for patient comfort (and/or to prevent a patient from moving e.g. shivering during scanning) is higher than a desired temperature range for detector cameras. Potentially, separating air circulating within a NMTS from air outside the system enables a larger temperature difference between a temperature of detector cameras and air temperature within the bore and/or room housing the NMTS.

In some embodiments, one or both of elements 412, 413 are temperature regulators, for example are configured to cool and/or heat e.g. air circulated through the temperature regulator. For example, in some embodiments, element 413 includes a heater configured to warm ambient air to a temperature range selected for patient comfort.

In some embodiments, warm air flowing out and cool air flowing into one or more detector unit 402 (e.g. each detector head) potentially mixes within housing 404. In some embodiments, flow of air through housing 404 is sufficient and/or a temperature of air within housing 404 is sufficiently low such that air drawn into detector unit/s cools the detector camera.

Alternatively or additionally to including a heat exchanger, in some embodiments element 415 includes one or more flow stabilizer and/or fluid control component. For example, including one or more fin and/or chamber and/or fan and/or baffle configured to guide and/or control flow of air through the housing. In some embodiments, the component includes one or more channel (e.g. channels 407, 425 as described and/or illustrated in FIG. 4B).

FIG. 4B is a simplified schematic of an imaging system 400 with closed loop cooling, according to some embodiments of the invention. Where, in some embodiments, imaging system 400 is an NMTS. In FIG. 4B, direction of fluid flow (e.g. air flow) at one or more point is illustrated by arrows.

In some embodiments, NMTS 400 includes separate channels within a detector carrier housing providing detector units with cool air and for accepting heated exhaust air from the detector units. For example, in some embodiments, a cool air inlet channel 425 is connected to an output of cooler 412 by an input pipe 418 and an exhaust channel 407 is connected to an input of cooler by an outlet pipe 416. In some embodiments, cool air from inlet channel 425 enters detector unit 402 and warmer air flows from the detector units into exhaust channel 407 e.g. for each detector unit. In some embodiments, the detector inlet and outlet channels 409, 411 are separated by a separator 469.

In some embodiments, one or both of channels 425, 407 rotate with a detector carrier 405 on which detector units 402 are mounted (e.g. rotation of the detector carrier and/or detector units as described elsewhere in this document). In some embodiments, cooler connection pipes 416, 418 are connected to fixed points of channels 425, 407, cooler connection pipes being sufficiently flexible and/or having sufficient slack to allow rotation of the detector unit e.g. by up to 360°, or up to 250°, or up to 180° or up to 100°-360° or lower or higher or intermediate ranges or angles.

In some embodiments, warm air is exhausted into a bore 414 of the NMTS e.g. from one or more detector unit and/or from channel 407 by one or more channel (not shown). Alternatively or alternatively, in some embodiments, a heat pump transfers heat from cooler 412 into bore 414. For example, in some embodiments, warm air generated by cooler 412 is exhausted into bore 414 e.g. through a channel 433. For example, when cooler 412 includes a compressor, heat generated by the compressor is transferred (e.g. by flow of air warmed by the compressor) to bore 414. Where heating of air within the bore potentially increases patient comfort.

FIG. 4C is a simplified schematic of an imaging system 400 with closed loop cooling, according to some embodiments of the invention. Where, in some embodiments, imaging system 400 is an NMTS. In FIG. 4C, direction of fluid flow (e.g. air flow) at one or more point is illustrated by arrows. In some embodiments, the NMTS illustrated in FIG. 4C includes one or more feature as described and/or as illustrated regarding FIGS. 4A-B.

In some embodiments, a cooler 412 is connected to one or more a heat exchanger 415 where heat exchanger 415 does not rotate with the detector carrier e.g. the heat exchanger is static. In some embodiments, heat exchanger 415 is a radiator supplied with coolant fluid by cooler 412 through pipes 416, 418. In some embodiments, heat exchanger 415 is an evaporator supplied with fluid by cooler 412 which includes a compressor. In some embodiments, heat exchanger 515 cools warm air within a detector exhaust channel 407, e.g. before the air returns to a detector input channel 425. In some embodiments, channels 407, 425 rotate with a detector carrier 414, heat exchanger 515, for example, accessing air within channel 425 through one or more slit in the channel. Alternatively or additionally, in some embodiments, one or more portion of channels 407, 425 are thermally coupled to heat exchanger 515, for cooling of the channels. Where, for example the thermal coupling is maintained when the channels 407, 425 rotate. In some embodiments, the channels 407 and 425 are separated from air within the detector carrier housing e.g. where separation prevents air flow between the channels and the detector carrier housing.

Figure 5:
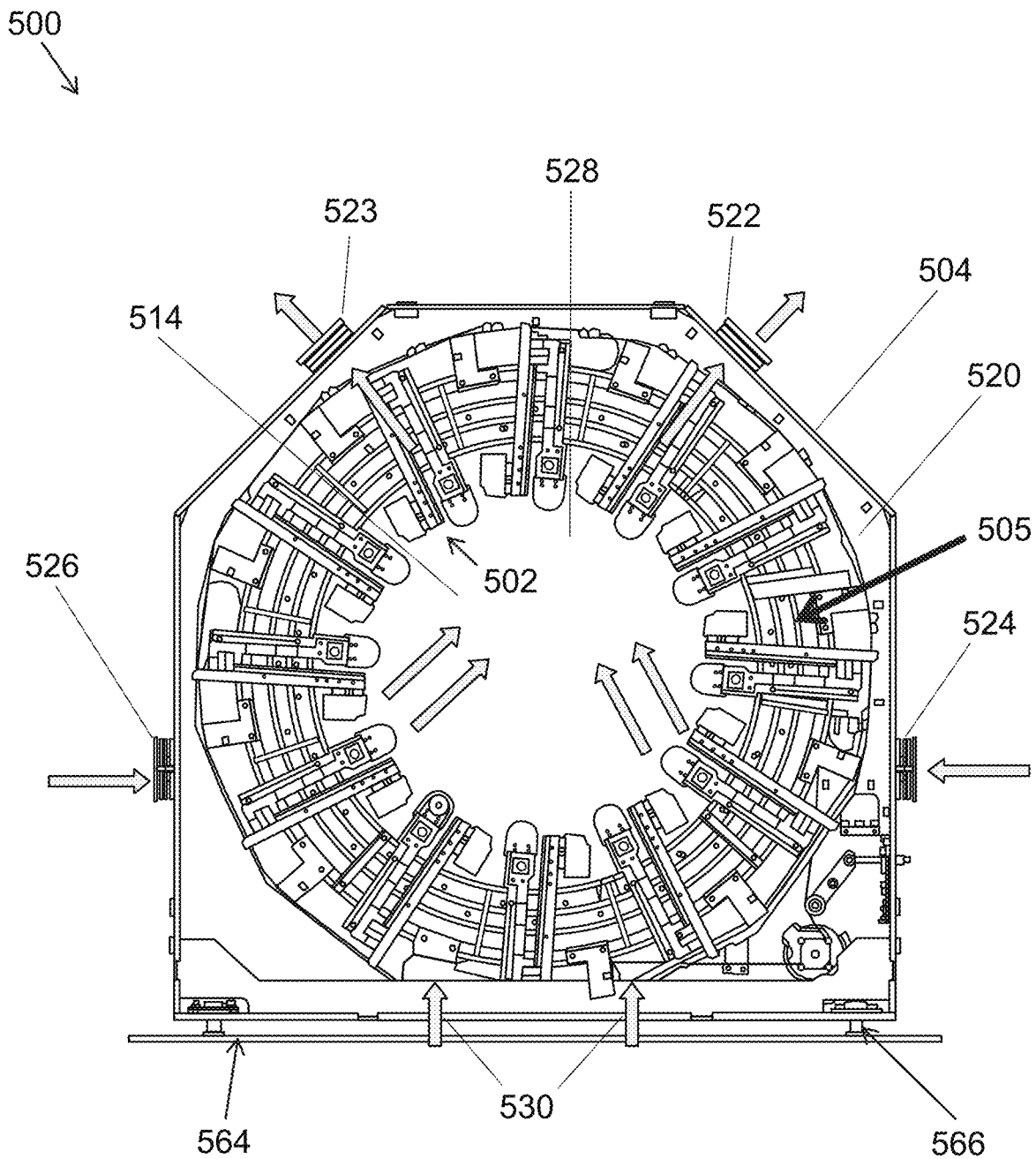
FIG. 5 is a simplified schematic side view of a NMTS including a plurality of cooling fans, according to some embodiments of the invention.

FIG. 5 is a simplified schematic side view of a NMTS 500 including a plurality of fans 522, 523, 524, 526, according to some embodiments of the invention. In FIG. 5 direction of fluid flow (e.g. air flow) at one or more point is illustrated by arrows.

Arrows illustrate exemplary direction of air flow within NMTS 500. In some embodiments, air is pulled into an inner space 520 (e.g. a base portion of inner space 520) of a NMTS housing 504 by one or more fan 524, 526. In some embodiments, air is pulled out of inner space 520 (e.g. at an upper portion of inner space) by one or more fan 522, 523. In some embodiments, housing 504 includes one or more inlet through which air enters and/or exits inner space 520 without being draw into the space by a fan and/or pump. For example, where air diffuses and/or flowing through (e.g. into) the inlet/s under pressure gradients e.g. due to movement of air by fan/s in other portions of the system.

In some embodiments, housing 504 sits on one or more foot 566. Where, in some embodiments, 564 is a floor surface (e.g. of a room in which the NMTS is located). In some embodiments, one or more foot 566 includes one or more wheel.

In some embodiments, warm air within a bore 514 of NMTS 500 (where the air is e.g. heated by portion/s of detector unit/s) rises upwards within the bore (e.g. as illustrated by arrows within the bore). In some embodiments, rising air from the bore passes into housing 504 and is exhausted away from the NMTS by one or more fan e.g. fans 522, 523.

Figure 6:
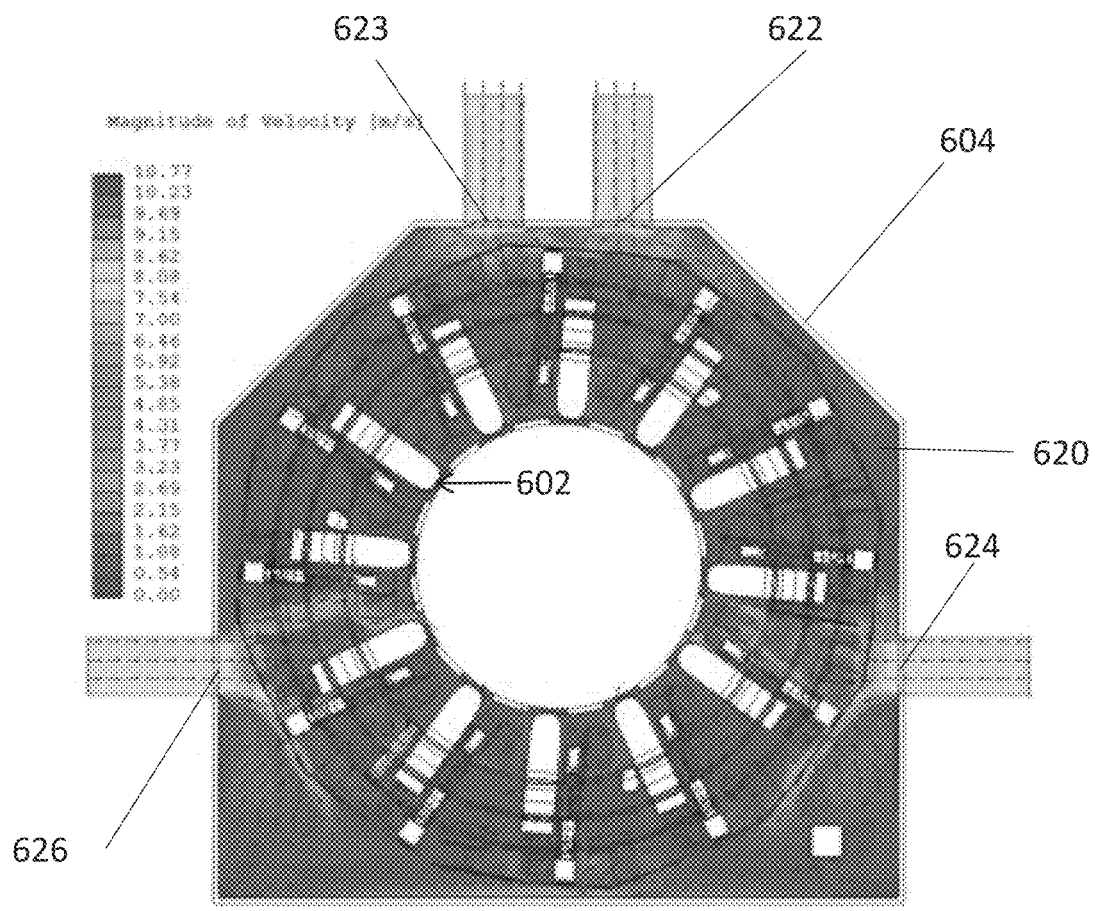
FIG. 6 is a simplified schematic cross sectional view of air velocity within a NMTS simulation results, according to some embodiments of the invention.

FIG. 6 is a simplified schematic cross sectional view of air velocity within a NMTS simulation results, according to some embodiments of the invention. In some embodiments, FIG. 6 illustrates air velocity within an NMTS where air velocity is higher at fan driven inlets 622, 623 and outlets 624, 626 as compared to air velocity within an inner space 620 of a NMTS housing 604.

FIGS. 7A-B are simplified schematic cross sectional views of simulation results for temperature within a NMTS, during operation of the NMTS, according to some embodiments of the invention.

FIG. 7A graphically illustrates a full range of temperatures for simulation results. FIG. 7A shows two higher temperature regions, a NMTS power source 732 and a motor 734. Where motor 734, in some embodiments, is configured to rotate the detector carrier.

FIG. 7B graphically illustrates temperatures under 30° C. In some embodiments, for functioning of detector camera/s, the detector camera arrays are required to be under a threshold of 30° C. FIG. 7B shows hotter regions around power source 732 and motor 734. Other regions are cooler including areas of an inner space 720 within a NMTS housing 704 around detector units 702.

Exemplary Cooling of Exemplary Detector Unit

FIG. 8 is a simplified schematic sectional view of an extendable arm 872, according to some embodiments of the invention. In FIG. 8 direction of fluid flow (e.g. air flow) at one or more point is illustrated by arrows.

In some embodiments, a distal portion of extendable arm 872 includes a detector head 873, where detector head 873 includes a detector camera 846. In some embodiments, e.g. as described regarding FIGS. 1C-D, extendable arm 872 is coupled to a chassis, forming a detector unit.

In some embodiments, detector camera 846 includes a collimator and a detector array 849. Where, for example, construction and/or operation of the collimator and/or array is as described in US Patent Publication No. 2015/0119704. In some embodiments, the collimator includes a plurality of septa e.g. constructed from tungsten and/or tungsten alloys. In some embodiments, the detector array is an array of cadmium zinc telluride (CZT) scintillator crystals. In some embodiments, scintillation is detected electronically e.g. without use of vacuum tubes.

In some embodiments, a detector camera is rotatable about one or more axis. In an exemplary embodiment, a detector camera is elongate in shape and rotates about a central long axis (e.g. axis 1047 of detector camera 1046, FIG. 10). In some embodiments, the detector camera is rotatable around more than one axis e.g. more than one actuator is configured to rotate the detector camera, e.g. each actuator rotating the detector camera around a different axis.

In some embodiments, rotation of the detector camera includes, oscillatory movement where the detector camera is rotated about a home position e.g. by 1-360° 1-300°, or 5-180° or 20-180° or lower or higher or intermediate ranges or angles about the home position (e.g. home position as illustrated in FIG. 10). In some embodiments, the home position is where the surface of the detector camera is perpendicular to a direction of extension of the extendable arm to which the detector camera is coupled.

In some embodiments, a detector unit includes one or more motor 838 (which is, for example, a stepper motor), configured to actuate rotation and/or oscillatory movement of the detector camera. In an exemplary embodiment, a motor is located at a longitudinal end of elongate detector camera 846. Alternatively or additionally, in some embodiments, one or more motor is located behind detector camera 846, e.g. located to a surface on an opposing side of the camera to the camera collimator.

In some embodiments, extendable arm 872 of a detector unit (e.g. includes one or more feature as described and/or illustrated regarding extendable arm of detector unit 102 FIGS. 1A-D) includes one or more space or hollow portion through which air flows e.g. to cool portion/s of the extendable arm and/or detector head.

In some embodiments, a detector unit includes one or more motor for actuation of movement of the extendable arm. In some embodiments, a motor 842 (e.g. a stepper motor) actuates movement of extendable arm 872 with respect to the detector carrier, e.g. moving the detector head on a rail (e.g. linear rail) mounted on a chassis coupled to the detector carrier. Where, in some embodiments, movement of the extendable arm with respect to the chassis is, e.g. as described regarding FIGS. 1C-D.

In some embodiments, detector head 873 includes one or more space or hollow portion. In some embodiments, extendable arm 872 includes a space 850 located behind a detector camera 846 where a flow of air (e.g. as illustrated by arrows) cool a surface 868 behind the detector array. In some embodiments, surface 868 includes a heat sink.

In some embodiments, air is pushed past surface 868 by an inlet fan 836. In some embodiments, air is pulled past surface 868 and through extendable arm 872 by one or more fan 844 located within a space 874 within the extendable arm. In some embodiments, space 874 extends into and/or is fluidly connected to a space within a NMTS housing (e.g. space 220 FIG. 2A, space 420 FIG. 4A).

In some embodiments, one or more fan (e.g. fan 836) is rotated with the detector camera e.g. is coupled to the detector camera and is rotated by an actuator (e.g. 836) configured to rotate the camera.

In some embodiments, air flow is directed across a length of surface 868 by a shape of spaces within the detector head. In some embodiments, detector head 873 includes a divider 840, which blocks air flow from inlet fan 836 from directly flowing up through space 874. In some embodiments, divider 840 is connected to a detector head housing, for example extending from an inner surface 878 of the detector head housing at region of the housing adjacent to space 874 and/or fan 836, in some embodiments, the divider is angled, extending towards surface 868 as the divider extends along a long axis of the detector head and/or camera e.g. reducing space 868 in a direction along the detector camera. Potentially, reducing space 868 increases air speed, potentially maintaining and/or increasing air speed in a direction from the fan towards the motor. A potential advantage being uniformity of temperature of surface 868 and/or detector camera 846. A further potential advantage being increased speed of air impinging on motor 838.

FIG. 9 is a simplified schematic cross sectional view of simulation results for air velocity within a detector unit 902, according to some embodiments of the invention.

FIG. 9 shows higher air speeds at the regions of fans 936, 944 and higher air speed at a region where the air flow impinges on a 938 motor (e.g. as described regarding air space 850 and/or motor 838 FIG. 8).

FIG. 9 illustrates an embodiment where a divider 940 is shaped such that air space 950 is reduced to a thin space where a dimension of the space in a direction parallel to a direction of extension of the extendable arm and/or parallel to a viewing direction of the detector camera is 0.5-10 mm, or 3-8 mm, or 5-6 mm, or lower or higher or intermediate ranges or distances.

FIG. 10 is a simplified schematic view of a detector unit 1002, according to some embodiments of the invention. In some embodiments, detector unit includes one or more feature as described and/or illustrated regarding other embodiments of detector units within this document e.g. detector unit 102 FIGS. 1A-D, detector unit 202 FIG. 2A, detector unit 402 FIGS. 4A-C.

In some embodiments, detector unit 1002 includes an extendable arm 1072 (e.g. including one or more feature described and/or illustrated regarding other embodiments of extendable arms within this document e.g. extendable arm 872 FIG. 8). In some embodiments, extendable arm 1072 is coupled to a chassis 1070 (where, for example, operation includes one or more feature as described and/or illustrated regarding extendable arm 172 and/or chassis 170 FIGS. 1A-D).

In some embodiments, detector head 1073 includes a cover 1060, which separates the head from bore air and/or protects the detector head. In some embodiments, cover 1060 includes thermally insulating material, e.g. to reduce bore air heating of the detector camera.

In some embodiments, detector unit 1002 is separated from ambient air, for example, for closed loop cooling (e.g. as described regarding FIG. 4A). Where, for example separation is between the detector unit and air within a bore (e.g. bore 114 FIGS. 1A-B). In some embodiments, a cover 1062 separates the detector unit and/or a portion of the detector unit (e.g. extendable arm 1072), for example from air within the bore. In some embodiments, cover 1062 is coupled to detector head cover 1060 e.g. covers detector head cover 1060.

In some embodiments, cover 1062 is extendable to maintain separation between the detector unit and bore air and/or cover the detector unit both when the extendable arm is extended and when the extendable arm is retracted. For example, in some embodiments, 1062 includes one or more expandable portion 1098 e.g. one or more elastically expandable portion and/or portion which unfurls and/or unfolds to expand. In an exemplary embodiment, expandable portion 1098 expands by unfolding concertina folds. In an exemplary embodiment, cover 1062 includes a first portion 1094 coupled to a distal end of the detector unit (e.g. distal end housing the detector camera), a second portion 1096 which covers a proximal portion of the detector unit (e.g. proximal portion where the detector unit is coupled to the detector carrier) and expandable portion 1098 couples first and second portions 1094, 1096. In some embodiments, the cover includes more than or less than three portions and/or more than one expandable portion. In some embodiments, the cover is formed from and/or includes portion/s constructed from fiber glass.

In some embodiments, where, for example, the system is a closed loop cooling system, air flow to cool the detector unit flows into the detector from an inner space of a detector carrier housing between cover 1062 and inner housings of the detector unit. Where the inner housings of the detector unit form a separation between the incoming and exhausting air flows (e.g. as described regarding separator 469 FIGS. 4A-B). Where flow of air back into the inner space is through a channel within the detector unit (e.g. as described elsewhere in this document).

FIG. 11 is a simplified schematic view of inner portions of a detector head, according to some embodiments of the invention.

In some embodiments, heat sink 1256 is coupled to detector camera 1146 by one or more clamp 1154, for example, by 1, or 2 or 3 (e.g. as illustrated in FIG. 11) or 3 or 4 or 5 or 1-10 or lower or higher or intermediate ranges or numbers of clamps. In some embodiments, a motor 1138 actuates rotation of detector camera 1156, e.g. by rotating an axle 1188 to which the detector camera is coupled. In some embodiments, heat sink 1256 is coupled to one side of axle 1188 and detector camera 1146 is coupled to the other side of axle e.g. the heat sink and detector camera opposing each other around the axle.

In some embodiments, a fan 1152 is positioned at and/or near a center of a length of detector camera 1146 and/or head sink 1156. For example, where fan 1152 is not located at a long axis end of the detector camera. In some embodiments, fan 1152 is directly coupled to detector camera 1146 and/or detector unit (including camera 1146 and heat sink 1156). In some embodiments, fan 1152 rotates with the detector camera, e.g. where rotation is actuated by one or more motor 1138, e.g. a stepper motor. In some embodiments, fan 1152 is in addition or is an alternative to a fan mounted on a detector unit housing and/or located at an end of a detector camera e.g. fan 836 FIG. 8.

Exemplary Detector Head Heat Sink

FIG. 12 is a simplified schematic of inner portions of a detector 1255 including a shaped heat sink 1256, according to some embodiments of the invention.

FIGS. 13A-B are simplified front views of portions of a detector camera unit 1355 within a detector cover 1360, according to some embodiments of the invention.

Referring now to FIG. 12, in some embodiments, a detector camera unit 1255 includes a heat sink 1256 coupled to detector camera 1246. In some embodiments, a detector camera 1246 includes a collimator 1280 and a detector array of scintillation crystals 1282 (e.g. as described elsewhere in this document).

In some embodiments, a plurality of detector camera units 1255 are each part of a different extendable arm coupled to a detector carrier (e.g. as described elsewhere in this document). In some embodiments, the extendable arms are translatable to bring two or more detector camera units into close proximity. Where close proximity between detector camera units includes contact between covers of the units (e.g. covers 1360 and 1376 FIG. 13B) and/or a distance between the two detector camera units at, at least one point of less than 20 mm, or less than 10 mm, or less than 5 mm, or 0.1 mm-20 mm, or 0.5 mm-3 mm, or lower or higher or intermediate ranges or distances.

In some embodiments, camera 1246 is movable (e.g. as described elsewhere in this document), for example, rotatable about one or more axis. In some embodiments, rotation of a detector camera unit reduces a distance between the detector camera unit and another detector camera unit, e.g. an adjacent detector camera unit. In some embodiments, heat sink 1256 is shaped to have reduced volume at one or more region which approaches adjacent detector camera unit/s during movement of the detector unit/s e.g. translation and/or rotation. In an exemplary embodiment, a detector camera unit is coupled to a heat sink with reduced volume at one or more portion of the detector camera unit, which rotates towards other detector camera unit/s.

In some embodiments, heat sink 1256 extends away from the detector camera, e.g. to a height above a surface (e.g. planar) of the detector camera. In some embodiments, the heat sink is shaped, e.g. including one or more portion which extends away from the detector camera to a lower height e.g. than other portion/s of the heat sink. The height reduction, in some embodiments, reducing one or more detector camera unit dimension for at least some angles of rotation of the detector about at least one axis. For example, referring now to FIGS. 13A-B, in some embodiments, the heat sink is shaped to reduce one or more moved and/or rotated dimension of the detector camera unit. In FIG. 13B a width of the detector camera unit, w3 is smaller in dimension to a width w4 of the detector camera unit with a heat sink which extends uniformly 1358.

In some embodiments, reduced height and/or lack of height uniformity of the heat sink reduces efficiency and/or or ability of the heat sink to cool the detector camera to a uniform temperature and/or ability of the heat sink to reduce temperature differences at different portions of the detector camera.

Returning now to FIG. 12, in some embodiments, heat sink 1256 opposes detector camera, for example with a planar surface of the heat sink parallel to a planar surface of the detector camera. In some embodiments, the detector array and/or collimator has a cuboid shape e.g. an elongate cuboid shape with a central long axis (e.g. as illustrated in FIG. 10; detector camera 1046 and/or axis 1047). In some embodiments, the heat sink has an elongate shape, in some embodiments, a long axis of the heat sink is parallel to a long axis of the detector camera.

In some embodiments the heat sink has a base portion 1290 (e.g. which is planar). In some embodiments, base portion 1290 is thermally coupled to the detector camera. In some embodiments, base portion 1290 has a top portion 1291, which opposes a top surface of the detector camera. In an exemplary embodiment, base portion 1290 has at least one side 1292 (e.g. two sides) which extend, from lateral edges of the base portion 1290 e.g. towards the detector camera 1246. In some embodiments, base portion 1290 is orientated parallel to one or more plane of the detector camera. Potentially, the base portion distributes heat, for example, potentially reducing variation in temperature of different portions of the detector camera and/or array.

In some embodiments, for example where the axis of rotation of the detector camera is parallel to a heat sink long axis, a cross section of the heat sink (e.g. cross section taken perpendicular to a long axis of the heat sink) is symmetrical.

In some embodiments, heat sink 1256 includes a plurality of fins 1284. In some embodiments, heat sink 1256 includes a plurality of fins 1284 separated by inlets 1286. In some embodiments, height of on outer contour of the heat sink (e.g. of fins) at one or more lateral edge and/or lateral portion (e.g. edge 2-50%, or 2-40%, or 2-10% or lower or higher or intermediate ranges or percentages of a width w1 of the heat sink) of the heat sink (h1 and/or h2) is 2-80%, or 2-50%, or 2-20%, or lower or higher or intermediate ranges or percentages of an average and/or maximum height of a central portion (e.g. a central 2-90% or 5-80%, or 4-40%) and/or tallest portion (e.g. height of a tallest fin, h3). In some embodiments, the heat sink is non-symmetrical, e.g. where h1 and h2 are not equal e.g. when the tallest portion of the heat sink (e.g. tallest fin) is not central on the cross section of the heat sink.

In some embodiments, the heat sink includes a portion, which extends away from the detector camera and/or planar portion 1290, which is, in some embodiments, has a non-cuboid shape.

In an exemplary embodiment, a shape of an outer contour of the heat sink curves away from a highest point (e.g. longest fin), fins, for example, gradually reducing in height away from the highest portion (e.g. longest fin). Where, in some embodiments, the outer contour is a smooth contour, which connects distal ends of heat sink fins. In some embodiments, a cross sectional shape of the heat sink e.g. of a contour contacting the tips of the fins is a curved shape e.g. an arc of a circle. In an exemplary embodiment, the shape is of an arc of a circle centered around the axis of rotation of the detector camera.

FIGS. 14A-C are simplified schematic exemplary detector camera unit cross sections, according to some embodiments of the invention. In some embodiments, the heat sink has other cross sectional outer contour shape/s, than those illustrated in FIGS. 12-13B, for at least a portion of the heat sink. For example, including fin/s which extend to a semi-circular shape (e.g. FIG. 14A), triangular shape (e.g. FIG. 14B), half polygon shape e.g. half pentagon, hexagon (e.g. FIG. 14C), heptagon, octagon.

In some embodiments, cross sectional shape of the heat sink changes along one or more axis of the heat sink (e.g. along a long axis of the heat sink and/or heat sink base), for example, in some embodiments, the heat sink includes one or more inlet configured to receive a clamp 1254. For example, in an embodiment where the detector camera has more than one axis of rotation, the heat sink is shaped along more than one cross section e.g. having a dome shape. In some embodiments, the heat sink has the same cross section (e.g. cross section perpendicular to a long axis of the heat sink and/or an axis of the heat sink parallel to an axis of rotation of the detector camera) for 70-98% of the length of the axis, or 85-95% or lower or higher or intermediate percentages or ranges. For examples, in some embodiments, the heat sink changing shape along a long axis of the heat sink, e.g. to maintain uniform temperature along the detector camera. For example, in some embodiment, the heat sink is taller at a region in proximity to a motor, which produces heat (e.g. motor 838 FIG. 8) and tapering and/or reducing along a long axis of the heat sink away from the motor.

In some embodiments, the detector camera embodiment illustrated in FIG. 12 has a single axis of rotation, which, in some embodiments, aligned with a long axis of detector camera 1246. In some embodiments, the axis of rotation is central with respect to a width w of the detector camera.

FIGS. 13A-B illustrate potential advantages of a shaped heat sink 1356 e.g. as described regarding heat sink 1256 FIG. 12. Potentially, the shaped heat sink (e.g. as compared to a cuboid cross section heat sink 1358) enables rotation of the detector camera within a smaller cover and/or a wider range of rotation angles for a given cover (e.g. without the heat sink contacting and/or experiencing high friction between the heat sink and the cover). A smaller cover potentially enables the detector camera to be positioned closer to a patient and/or a region of interest e.g. within a patient. Potentially, shaped cover 1356 enables detector head 1373 to be advanced closer to another detector head 1376 e.g. for a smaller bore size.

General

It is expected that during the life of a patent maturing from this application many relevant nuclear medicine technologies will be developed and the scope of the terms nuclear medicine tomography system, cooling system, detector head, heat sink, are intended to include all such new technologies a priori. As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first, indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A nuclear medicine tomography system comprising:
   a detector carrier;
   a detector carrier housing including an inner space;
   a heat pump configured to cool air within said inner space to a temperature below a room temperature of a room in which said nuclear medicine tomography system is located; and
   a plurality of detector units, coupled to said detector carrier, each detector unit comprising:
   a detector camera;

a cooling channel, which guides the air to the detector camera from said inner space; and an exhaust channel, which guides the air from the detector camera to said inner space;

at least one sensor configured to generate a signal based on a temperature at one or more points within said nuclear medicine tomography system; and a processor;

wherein said heat pump comprises at least one actuator;

wherein said processor comprises circuitry configured to send a control signal to said at least one actuator, said heat pump configured to maintain a temperature of said detector camera of at least one of said plurality of detector units below a threshold temperature.

2. The nuclear medicine tomography system according to claim 1, wherein each detector unit further comprises an extendable arm in which said detector camera is housed;

wherein said cooling channel and said exhaust channel pass through said extendable arm.

3. The nuclear medicine tomography system (NMTS) according to claim 1, further including a room temperature regulator configured to control a room temperature of a room in which said nuclear medicine tomography system is housed, said room temperature regulator having at least one actuator; and wherein said processor is further configured to send a room control signal configured to control said at least one actuator of said room temperature regulator to maintain said room temperature of the room within a temperature range selected for patient comfort.

4. The nuclear medicine tomography system according to claim 3, wherein said threshold temperature is below a lowest bound of said temperature range.

5. The nuclear medicine tomography system according to claim 4, wherein said lowest bound of said temperature range is 23° C.

6. The nuclear medicine tomography system according to claim 4, wherein said lowest bound of said temperature range is 25° C.

7. The nuclear medicine tomography system according to claim 1, further comprising at least one actuator configured to generate an air flow through one or both of said cooling channel and said exhaust channel of each of said plurality of detector units.

8. The nuclear medicine tomography system according to claim 1, further comprising a second surface coupled to said detector camera, wherein said detector camera includes a detector camera surface, and wherein said exhaust channel extends along said detector camera surface or along said second surface.

9. The nuclear medicine tomography system according to claim 1, further comprising a motor configured to actuate a movement of said detector camera, wherein said motor includes a motor housing; and wherein said exhaust channel is shaped to increase a volumetric fluid flow rate impinging said motor housing.

10. The nuclear medicine tomography system according to claim 1, wherein said heat pump comprises an air conditioner configured to deliver cooled air to said inner space.

11. The nuclear medicine tomography system according to claim 1, wherein said cooling channel and said exhaust channel are separated from each other.

12. The nuclear medicine tomography system according to claim 1, further comprising at least one fan configured to circulate air within said inner space.

13. The nuclear medicine tomography system according to claim 1, further comprising a detector carrier motor configured to rotate said detector carrier within said detector carrier housing.

14. The nuclear medicine tomography system according to claim 1, wherein each of said plurality of detector units further comprises at least one sensor and an actuator, wherein said processor is further configured to generate a control signal for the detector camera of each of said plurality of detector units, based on a measurement signal from said at least one sensor associated with each of said plurality of detector units, and to send the control signal for each of said plurality of detector units to said actuator associated with the respective one of plurality of detector units.

15. A nuclear medicine tomography system comprising:

a detector carrier;

a detector carrier housing including an inner space;

a heat pump configured to cool air within said inner space to a temperature below a room temperature of a room in which said nuclear medicine tomography system is located; and a plurality of detector units, coupled to said detector carrier, each detector unit comprising:

a detector camera;

a cooling channel, which guides the air to the detector camera from said inner space; and an exhaust channel, which guides the air from the detector camera to said inner space;

wherein said heat pump comprises a portion located within said detector carrier housing.

16. A nuclear medicine tomography system comprising:

a detector carrier;

a detector carrier housing including an inner space;

a heat pump configured to cool air within said inner space to a temperature below a room temperature of a room in which said nuclear medicine tomography system is located; and a plurality of detector units, coupled to said detector carrier, each detector unit comprising:

a detector camera;

a cooling channel, which guides the air to the detector camera from said inner space; and an exhaust channel, which guides the air from the detector camera to said inner space;

wherein at least one of said plurality of detector units comprises a rotation actuator configured to rotate said detector camera of said at least one of said plurality of detector units; and wherein said rotation actuator is configured to actuate an oscillatory rotation of said detector camera of said at least one of said plurality of detector units.

17. A nuclear medicine tomography system comprising a detector carrier;

a detector carrier housing including an inner space;

a heat pump configured to cool air within said inner space to a temperature below a room temperature of a room in which said nuclear medicine tomography system is located; and a plurality of detector units, coupled to said detector carrier, each detector unit comprising:

a detector camera;

a cooling channel, which guides the air to the detector camera from said inner space; and an exhaust channel, which guides the air from the detector camera to said inner space; and a bore, wherein at least one of said plurality of detector units includes a layer of thermal insulation configured to reduce a heat transfer to said detector camera of said at least one of said plurality of detector units from said bore.

18. A method of setting a room temperature comprising:

setting a desired room temperature, which is above a threshold temperature of 23° C. and is selected for patient comfort; and setting a desired temperature of a detector camera of a nuclear medicine tomography system (NMTS), wherein the desired temperature is selected for a low noise of said detector camera and is below said desired room temperature.

19. The method according to claim 18, wherein said setting a desired temperature of a detector camera of a nuclear medicine tomography system (NMTS) comprises sending a control signal to a heat pump.

\* \* \* \* \*